United States Patent
Golz et al.

(10) Patent No.: US 9,943,522 B2
(45) Date of Patent: Apr. 17, 2018

(54) USE OF CATHEPSIN K INHIBITION FOR THE TREATMENT AND/OR PROPHYLAXIS OF PULMONARY HYPERTENSION AND/OR HEART FAILURE

(75) Inventors: Stefan Golz, Mülheim an der Ruhr (DE); Martina Delbeck, Heiligenhaus (DE); Heinrich Meier, Wuppertal (DE); Andreas Geerts, Wuppertal (DE); Thomas Mondritzki, Schwelm (DE); Hubert Trübel, Wuppertal (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 21 days.

(21) Appl. No.: 14/118,222

(22) PCT Filed: May 11, 2012

(86) PCT No.: PCT/EP2012/058773
§ 371 (c)(1),
(2), (4) Date: Jan. 10, 2014

(87) PCT Pub. No.: WO2012/156311
PCT Pub. Date: Nov. 22, 2012

(65) Prior Publication Data
US 2014/0155383 A1 Jun. 5, 2014

(30) Foreign Application Priority Data
May 16, 2011 (EP) .................... 11166229

(51) Int. Cl.
| A61K 31/55 | (2006.01) |
|---|---|
| A61K 31/277 | (2006.01) |
| A61K 31/336 | (2006.01) |
| A61K 31/40 | (2006.01) |
| A61K 31/495 | (2006.01) |
| A61K 31/165 | (2006.01) |

(Continued)

(52) U.S. Cl.
CPC ............ *A61K 31/55* (2013.01); *A61K 31/165* (2013.01); *A61K 31/277* (2013.01); *A61K 31/336* (2013.01); *A61K 31/40* (2013.01); *A61K 31/415* (2013.01); *A61K 31/495* (2013.01); *A61K 31/496* (2013.01)

(58) Field of Classification Search
CPC .............................. A61K 31/55; A61K 31/495
USPC .......................... 514/254.02, 212.08, 252.12
See application file for complete search history.

(56) References Cited

U.S. PATENT DOCUMENTS

| 7,375,134 B2 * | 5/2008 | Bayly | ................... C07C 255/25 |
|---|---|---|---|
| | | | 514/252.01 |
| 2009/0005323 A1 * | 1/2009 | Percival | ............... A61K 31/277 |
| | | | 514/23 |

FOREIGN PATENT DOCUMENTS

| JP | 2006-503810 A | 2/2006 |
|---|---|---|
| WO | 99/11640 A1 | 3/1999 |
| WO | 00/38687 A1 | 7/2000 |

(Continued)

OTHER PUBLICATIONS

Kaw, British Journal of Medical Practitioners, Jun. 2009;2(2):4-5.*

(Continued)

*Primary Examiner* — San Ming R Hui
(74) *Attorney, Agent, or Firm* — Morrison & Foerster LLP

(57) ABSTRACT

The present invention relates to the use of cathepsin K and/or cathepsin S inhibitors in a method for the treatment and/or prophylaxis of pulmonary hypertension and/or heart failure.

6 Claims, 4 Drawing Sheets

Right Ventricular Hypertrophy

(51) Int. Cl.
*A61K 31/415* (2006.01)
*A61K 31/496* (2006.01)

(56) References Cited

FOREIGN PATENT DOCUMENTS

| WO | 00/55126 | A2 | 9/2000 |
|---|---|---|---|
| WO | 01/58886 | A1 | 8/2001 |
| WO | 01/70232 | A1 | 9/2001 |
| WO | 02/068579 | A2 | 9/2002 |
| WO | 03/075836 | A2 | 9/2003 |
| WO | 2004/007477 | A1 | 1/2004 |
| WO | 2004/058238 | A1 | 7/2004 |
| WO | 2004/075835 | A2 | 9/2004 |
| WO | 2004/096785 | A1 | 11/2004 |
| WO | 2006/076797 | A1 | 7/2006 |
| WO | 2006076796 | A1 | 7/2006 |
| WO | WO2006/076797 | * | 7/2006 |
| WO | 2007/003056 | A1 | 1/2007 |
| WO | 2009/129546 | A1 | 10/2009 |
| WO | 2010/011605 | A2 | 1/2010 |
| WO | 2010/011782 | A1 | 1/2010 |
| WO | 2012/156311 | A1 | 11/2012 |

OTHER PUBLICATIONS

Stenmark et al., "Animal models of pulmonary arterial hypertension: the hope for etiological discovery and pharmacological cure," American Journal Physiol. Lung Cell Mol. Physiol., Sep. 11, 2009, 297:L1013-L1032.
Bone et al., "Odanacatib, a Cathepsin-K Inhibitor for Osteoporosis: A Two-Year Study in Postmenopausal Women With Low Bone Density," Journal of Bone and Mineral Research, May 2010, 25(5):937-947.
Campian et al., "How valid are animal models to evaluate treatments for pulmonary hypertension?" Naunyn-Schmiedeberg's Archives of Pharmacology, 2006, 373:391-400.
Heinke et al., "Apoptosis of ventricular and atrial myocytes from pacing-induced canine heart failure," Cardiovascular Research, 2001-49:127-134.
Yap et al. "Natriuretic Peptides, Respiratory Disease, and the Right Heart," Chest, Oct. 2004, 126(4):1330-1336.
Ishii et al., "Plasma concentration of brain natriuretic peptide as a biochemical marker for the evaluation of right ventricular overload and mortality in chronic respiratory disease," Clinica Chimica Acta, 2000, 301:19-30.
Volpe et al., "Prediction of Long-Term Survival in Chronic Heart Failure by Multiple Biomarker Assessment: A 15-Year Prospective Follow-Up Study," Clinical Cardiology, 2010, 33(11):700-707.
D'Alonzo et al., "Survival in Patients with Primary Pulmonary Hyprtension," Annals of Internal Medicine, Sep. 1, 1991, 115(5):343-349.
Euler et al., "Observations on the Pulmonary Arterial Blood Pressure in the Cat.," Acta Physiol. Scandinav., 1946, 12:301-320.
Gauthier et al., "The discovery of odanacatib (MK-0822), a selective inhibitor of cathepsin K," Bioorganic & Medicinal Chemistry Letters, 2008, 18:923-928.
Ghofrani et al., "Neue Therapieoptionen in der Behandlung der pulmonalarteriellen Hypertonie," Herz, 2005, 30(4):296-302.
Tanaka et al., "Pharmacogenomics of Cardiovascular Pharmacology: Pharmacogenomic Network of Cardiovascular Disease Models," Journal of Pharmacological Sciences, 2008, 107:8-14.
Thompson et al., "Chronic hypoxic pulmonary hypertension in the guinea pig: effect of three levels of hypoxia," Journal of Applied Physiology, Feb. 1, 1993, 74(2):916-921.
Lecaille et al., "Biochemical properties and regulation of cathepsin K activity," Biochimie, 2008, 90:208-226.
Li et al., "Identification of a potent and selective non-basic cathepsin K inhibitor," Bioorganic & Medicinal Chemistry Letters, 2006-15:1985-1989.
Marquis et al., "Azepanone-Based Inhibitors of Human and Rat Cathepsin K," Journal of Medicinal Chemistry, 2001, 44(9):1380-1395.
Mondritzki et al. "Differentiation of Arginine Vasopressin Antagonistic Effects by Selective V2 versus Dual V2/V1a Receptor Blockade in a Preclinical Heart Failure Model," American Journal of Therapeutics, 2011, 18(1):31-37.
O'Shea et al., "A Practical Enantioselective Synthesis of Odanacatib, a Potent Cathepsin K Inhibitor, via Triflate Displacement of an α-Trifluoromethylbenzyl Triflate," Journal of Organic Chemistry, 2009, 74(4):1605-1610.
Palmer et al., "Design and Synthesis of Tri-Ring P3 Benzamide-Containing Aminonitriles as Potent, Selective, Orally Effective Inhibitors of Cathepsin K," Journal of Medicinal Chemistry, 2005, 48(24):7520-7534.
Pfeifer et al., "ANP gene expression in rat hearts during hypoxia," Pflügers Archiv—European Journal of Physiology, 1997, 434:63-69.
Jeffery et al., "Pulmonary vascular remodeling: a target for therapeutic intervention in pulmonary hypertension," Pharmacology & Therapeutics, 2001-92:1-20.
Robichaud et al., "Identification of a Nonbasic, Nitrile-Containing Cathepsin K Inhibitor (MK-1256) that is Efficacious in a Monkey Model of Osteoporosis," Journal of Medicinal Chemistry, 2008, 51(20):6410-6420.
Sinha et al., "Expression of latent TGF-beta binding proteins and association with TGF-beta1 and fibrillin-1 following arterial injury," Cardiovascular Research, 2002, 53:971-983.
Truppo, M. D., "An Efficient, Asymmetric Synthesis of Odanacatib, a Selective Inhibitor of Cathepsin K for the Treatment of Osteoporosis, Using an Enzyme-Mediated Dynamic Kinetic Resolution," H. U. Blaser, H-J. Federsel, Asymmetric catalysis on industrial scale, 2nd. Edition, 2010, 397-414.
Veillard et al., "Lung cysteine cathepsins: Intruders or unorthodox contributors to the kallikrein-kinin system?," The International Journal of Biochemistry & Cell Biology, 2008-40:1079-1094.
Voelkel et al., "Hypoxia-induced pulmonary vascular remodeling: a model for what human disease?," The Journal of Clinical Investigation, Sep. 2000, 106(6):733-738.
Watkins et al., "A direct interaction between TGFβ activated kinase 1 and the TGF type II receptor: Implications for TGFh signalling and cardiac hypertrophy," Cardiovascular Research, 2006, 69:432-439.
Weissmann et al., "Hypoxic pulmonary vasoconstriction: a multifactorial response?," American Journal of Physiology Lung Cellular and Molecular Physiology, 2001, 281:L314-L317.
Yamashita et al., "Structure Activity Relationships of 5-, 6-, and 7-Methyl-Substituted Azepan-3-one Cathepsin K Inhibitors," Journal of Medicinal Chemistry, 2006, 49(5):1597-1612.
Yatsu et al., "Effect of Conivaptan, A combined Vasopressin V1a and V2 Receptor Antagonist, on Vasopressin-Induced Cardia and Haemodynamic Changes in Anaesthetised Dogs," Pharmacological Research, 2002, 46(5):375-381.
Zhao et al., "Cathepsin K: A therapeutic target for bone diseases," Biochemical and Biophysical Research Communications, 2009, 380:721-723.
Potter et al., "Natriuretic Peptides: Their Structures, Receptors, Physiologic Functions and Therapeutic Applications," Handbook of Experimental Pharmacology 191, 2009, 341-366.
European Patent Office, Written Opinion for International Patent Application No. PCT/EP2012/058773, Nov. 16, 2013, 10 pages.
European Patent Office, International Search Report for International Patent Application No. PCT/EP2012/058773, Jun. 22, 2012, 7 pages.
International Bureau of WIPO, International Preliminary Report on Patentability for International Patent Application No. PCT/EP2012/058773, Nov. 19, 2013, 11 pages.

* cited by examiner

USE OF CATHEPSIN K INHIBITION FOR THE TREATMENT AND/OR PROPHYLAXIS OF PULMONARY HYPERTENSION AND/OR HEART FAILURE

CROSS REFERENCE TO RELATED APPLICATIONS

This application is the national stage of International Application No. PCT/EP2012/058773, filed internationally on May 11, 2012, which claims the benefit of European Application No. 11166229.2, filed on May 16, 2011.

The present invention relates to the use of cathepsin K and/or cathepsin S inhibitors in a method for the treatment and/or prophylaxis of pulmonary hypertension and/or heart failure.

BACKGROUND OF THE INVENTION

Cathepsin Proteases

Cathepsins (Ancient Greek kata-"down" and hepsein "boil"; abbreviated CTS) are proteases: proteins that break apart other proteins, found in many types of cells including those in all animals. There are approximately a dozen members of this family, which are distinguished by their structure, catalytic mechanism, and which proteins they cleave. Most of the members become activated at the low pH found in lysosomes. Thus, the activity of this family lies almost entirely within those organelles. Cathepsins have a vital role in mammalian cellular turnover, e.g. bone resorption. They degrade polypeptides and are distinguished by their substrate specificites.

The complete sequence of the human genome, published in 2003, encode total of 11 cysteine cathepsins (B, H, L, S, C, K, O, F, V, X and W). These, which are also known as lysosomal proteases, belong to the papain-like protease family.

Cathepsins are described as involved in: cancer, stroke, Alzheimer's disease, Arthritis, Ebola, (Cathepsin L and to a lesser extent cathepsin B have been found to be necessary for the virus to enter host cells), COPD, chronic periodontitis, and several ocular disorders: keratoconus, retinal detachment, age-related macular degeneration, glaucoma and others.

Cathepsin K (CTSK)

Cathepsin K (genbank accession no: NM_000396.3 (polynucleotide) and NP_000387.1 (polypeptide)), abbreviated CTSK, is an enzyme which in humans is encoded by the CTSK gene. The protein encoded by this gene is a lysosomal cysteine protease involved in bone remodeling and resorption. This protein, which is a member of the peptidase C1 protein family, is predominantly expressed in osteoclasts.

Human cathepsin K is encoded by approximately 12.1 kb of genomic DNA and is mapped to chromosome 1q21. Analysis of the genome DNA sequence indicates eight exons and seven introns locate in the gene. The transcription product is 1.7 kb long. No TATA/CAAT box has been found at the 50 end of the transcriptional initiation start, but two consensus Sp1 binding sites and a rich GtC region (42.5%) are identified in the promoter region as potential regulatory elements. Primer extension analysis indicates the transcription start site located at the 58 bp upstream of methionine. Initiation of transcription may be enhanced by several putative transcription regulatory elements: AP1, AP3, H-APF-1, PU.1, ETS-1, PEA3, Mitf, TFE3. Cathepsin K is synthesized as an inactive pre-proenzyme which contains 329 amino acids (aa) with the molecular weight 38 ku. It includes a 15-amino acid signal sequence, a 99-amino acidpropeptide and the overall organization of the catalytic site. The catalytic site consists of two domains folded together to give a "V"-shaped active site cleft configuration. The central helix is the most prominent feature of the left domain, whereas the right domain is mostly dominated by b-barrel motifs. The active site lies at the interface between the two domains. The pro-peptide contains a conserved N-glycosylation site which may target the inactive proenzyme to lysosomes via the mannose 6-phosphate receptor pathway. The pro-peptide of 99 aa is cleaved between Arg114 and Ala115 into a mature form of 215 amino acids [1]. Cysteine cathepsins are not strictly lysosomal, the proteases are transported between phagosomes, endosomes and lysosomes, and individual enzymes may accumulate in certain organelles under specific physiological circumstances. Cysteine cathepsins are also released into the cytoplasm after lysosomal leakage caused by exogenous oxidants (reactive oxygen species).

Cathepsin K is a protease, which is defined by its high specificity for kinins, that is involved in bone resorption. The enzyme's ability to catabolize elastin, collagen, and gelatin allow it to break down bone and cartilage. This catabolic activity is also partially responsible for the loss of lung elasticity and recoil in emphysema. Cathepsin K inhibitors, such as odanacatib, show great potential in the treatment of osteoporosis. Cathepsin K is also expressed in a significant fraction of human breast cancers, where it could contribute to tumor invasiveness. Mutations in this gene are the cause of pycnodysostosis, an autosomal recessive disease characterized by osteosclerosis and short stature. Cathepsin K expression is stimulated by inflammatory cytokines that are released after tissue injury.

Regulation of CTSK

During osteoclast differentiation, osteoblasts/stromal cells produce cytokines including macrophage-colony-stimulating factor (M-CSF) and receptor activator of NF-jB ligand (RANKL) that induce and modulate growth and differentiation of the precursor to mature osteoclasts. Intracellular RANK signaling by its interaction with RANKL induces recruitment and activation of cytoplasmic tumor necrosis factor receptor-associated factors (TRAFs), leading to the activation of multiple signaling cascades such as MAPK, NF-jB, Src, and Akt. RANKL could stimulate CTSK expression and promoter activity in a dose- and time-dependent manner. A large number of agents regulate the production of RANKL by osteoblasts and stromal cells could also regulate the expression of cathepsin K. Stimulators include vitamin D, parathyroid hormone, TNF-a, glucocorticoids, IL-1, IL-11, thyroid hormone, prostaglandin E2, lipopolysaccharide, fibroblast growth factor-2, histamine, insulinlike growth factor-1, histamine, and low gravity. Inhibitors of RANKL expression include estrogen and transforming growth factor-b. RANKL appears to stimulate the transcription of the cathepsin K gene via a number of mechanisms. An early and proximal event in RANKL-mediated signaling involves activation of TRAF6, which is a critical adaptor molecule for the cognate receptor of RANKL. Overexpression of TRAF6 stimulates cathepsin K promotor activity, and RANKL stimulation of cathepsin K promotor activity is inhibited by the overexpression of dominant negative TRAF6. The activation of cathepsin K by RANKL could also be inhibited by dominant negative c-fos. JunB alone stimulated basal cathepsin K promoter activity, whereas c-jun, JunD or c-fos alone did not. However, cotransfection of any of these jun-family members with c-fos (AP-1) significantly increased cathepsin K promoter expression.

siRNA targeted against c-jun or junB suppressed RANKL-mediated cathepsin K expression, Therefore, AP-1 help regulate the basal and RANKL-mediated stimulation of cathepsin K gene expression. More distally in the signaling pathway, RANKL could lead to the phosphorylation of NFAT2 by p38, thereby inducing translocation of NFAT2 into the nucleus and subsequent transactivation of the human cathepsin K promoter. This phosphorylation of NFAT2 contrasts with the classical paradigm whereby calcineurin dephosphorylates both NFAT1 and NFAT2, leading to nuclear translocation and subsequent promotor activation of a spectrum of genes. However, it is possible that both dephosphorylation and phosphorylation of different moieties of NFAT2 may induce translocation and subsequent transactivation of transcription. RANKL treatment of cells also induces phosphorylation of the microphthalmia transcription factor (Mite via p38. Mitf could bind to three E-box motifs in the human cathepsin K promoter. Overexpression of wildtype Mitf in cultured osteoclasts significantly enhanced cathepsin K expression. Additional agents active in bone physiology could also stimulate cathepsin K expression, such as retinoic acid, intermittent mechanical stretching and extracellular matrix proteins (collagen type I, fibronectin, vitronectin, osteopontin). Physiological inhibitors of osteoclast differentiation and activation, such as OPG, IL-6, INF-c, can also directly suppress cathepsin K expression [1].

Human CTSK Polymophisms

The important role of cathepsin K in osteoclast function was first suggested by the finding that mutations in this gene could cause pycnodysostosis. The human disorder pycnodysostosis is a rare, autosomal, recessive, skeletal disorder caused by mutations in cathepsin K. At present, we have identified six different mutations in human beings: (1) an A-G transition at cDNA position 1095 (2) a G-C transition at nucleotide 541 (3) a C-T transition at nucleotide (4) a C-T transition at nucleotide 935 (5) a G-A transition at nucleotide 236 (6) a T-C transition at nucleotide 926. Mutation in these genes affects the metabolism of the skeletal system, causing defects in bone resorption and bone remodeling. In clinics, pycnodysostosis is characterized by short stature, osteosclerosis, acroosteolysis, spondylolysis, separated cranial sutures with open fontanelles, bone fragility, and loss of mandibular angle. The cathepsin K mutation causes unique pycnodysostosis disorders rather than simple osteopetrosis, as seen in other diseases associated with osteoclast genes, such as c-src or Atp6i. This feature of the cathepsin K mutation along with the detection of cathepsin K mRNA in a variety of tissues including bone, ovary, heart, placenta, lung, skeletal muscle, colon and small intestine suggest that cathepsin K may constitute other functions beyond just matrix protein degradation that may result in the unique phenotypes of pycnodysostosis [1].

Catalytic Mechanism

The catalytic triad of cathepsin K (Cys25, His159, Asn175, papain numbering) is classically housed in a cleft separating the two domains, with Cys25 located in a long, conserved, N-terminal a-helix of the left domain, whereas His159 is in the other domain. Cys25 and His159 are believed to exist as the thiolateeimidazolium ion pair which is stabilized by Asn175 via a hydrogen bond with His159. The cysteine sulfhydryl group is partly responsible for the low pKa (w3.7). Briefly, the thiolate anion attacks the carbonyl carbon of the substrate bond to be cleaved to form a tetrahedral intermediate. This intermediate is first stabilized by the oxyanion hole and then transformed into an acyl enzyme with the release of the protonated leaving amine. A nucleophilic attack by a water molecule results in the formation of second tetrahedral intermediate. This finally splits to generate the free enzyme and the second portion (R—COOH) of the substrate [2].

Substrate Specificity

Most C1 cysteine cathepsins are endopeptidases (L, S, K, V, F), while cathepsin X is a carboxypeptidase and cathepsins B, C and H have both endopeptidase- and exopeptidase activities. The substrate-binding region of cysteine cathepsins is defined as an arrangement of binding subsites (SeS0) for peptide substrate amino acids (PeP0) on both sides (N- and C-) of the scissile bond, encompassing the stretch of seven sites from S4 to S30 of papain. Since the crystal structure of numerous substrate analogue inhibitors are available, the definition has been revised and redefined, limiting the binding of substrate residues to subsites S2eS10, in which both main-chain and side-chain atoms are involved. However recent studies have shown the importance of cathepsin K site S3 for determining substrate specificity. Whereas the S2 binding site is a true deep pocket, the other sites provide a binding surface. Furthermore, while S2 and S10 sites are the major determinants of specificity, S1 is important for the affinity and efficient catalysis of substrates. The positioning of the P3 residue in site S3 is, as in subsite S20, mediated only by side chain contacts over a relative wide area. Cathepsins K, L, S and V have partly overlapping specificities, making it difficult to discriminate between them in vivo. Cathepsin K attacks sites having aliphatic amino acids (Leu, Ile, Val), unlike cathepsins L and V (which both rather accept hydrophobic residues with preference for Phe), and also accommodates Pro in the S2 subsite. Cathepsin K is unusual among cysteine cathepsins in that it can cleave substrates with Pro in the P2 position, although it has been reported that congopain, a cysteine protease from Trypanosoma congolense, with an amino acid sequence (65% of homology) and biochemical properties similar to cathepsin K, also does so. Another feature of cathepsin K is its preference for Gly at the P3 position [2].

Tissues and Cellular Distribution

Cysteine cathepsins are not strictly lysosomal, the proteases are transported between phagosomes, endosomes and lysosomes, and individual enzymes may accumulate in certain organelles under specific physiological circumstances. Cysteine cathepsins are also released into the cytoplasm after lysosomal leakage caused by exogenous oxidants (reactive oxygen species). Acidification of the pericellular space of monocyte-derived macrophages, lung macrophages and osteoclasts enhances the release of cathepsin K to promote extracellular proteolysis. An Hp-ATPase pump may be involved in the production of an acidic subcellular space by transferring protons from the cytoplasmic to the extracellular space. Immunolocalization, in situ hybridization and fluorescence microscope studies have shown that cathepsin K is much more abundant in osteoclasts along the bone resorption lacunae than are cathepsins B, L and S. Cathepsin K mRNA has been detected in a variety of tissues including bone, ovary, heart, placenta, lung, skeletal muscle, colon and small intestine. High concentrations of cathepsin K have been found in osteoclasts, osteoclast-like cells (giant multinucleated cells) and also in synovial fibroblasts and in rheumatoid arthritic joints, which are involved in the pathological erosion of articular cartilage, and in epithelioid cells of organ systems like the lung and thyroid gland. Cathepsin K is also found in aortic smooth muscle cells, macrophages, in bronchoalveolar fluids, and is secreted by macrophages, which could be of considerable importance for the remodeling of the extracellular matrix [2].

Cathepsin S (CTSS)

Cathepsin S, also known as CTSS, is a protein which in humans is encoded by the CTSS gene (Gene ID: 1520). The protein encoded by this gene, a member of the peptidase C1 family, is a lysosomal cysteine protease that may participate in the degradation of antigenic proteins to peptides for presentation on MHC class II molecules. The encoded protein can function as an elastase over a broad pH range in alveolar macrophages. Transcript variants utilizing alternative polyadenylation signals exist for this gene. Cathepsin S has been shown to be a significant prognostic factor for patients with type IV astrocytomas (glioblastoma multiforme) and its inhibition has shown improvement in survival time by mean average 5 months. This is because the cysteine enzyme can no longer act together with other proteases to break up the brain extracellular matrix. So the spread of the tumor is halted.

CTSK Inhibitors

Cathepsin K inhibitors are widely described in literature, but not limited to, the treatment of bone diseases.

WO 2004/007477 describes acyl hydrazino thiophene derivatives as inhibitors for metabolic enzymes (i.a. Cathepsin K) amongst others for the treatment of cardiovascular diseases. WO 2006/076796 mentions Cathepsin K inhibitors may be useful for the treatment of obesity and related disorders.

Odanacatib, a selctive Cathepsin K inhibitor, and its use for the treatment of osteoporosis is described in J. Bone Miner. Res. 25 (5) 937-947 (2010).

The present invention relates to the use of, preferably selective, Cathepsin K inhibitors in the treatment and/or prophylaxis of pulmonary hypertension and heart failure, and to the use thereof in the treatment and/or prophylaxis of pulmonary hypertension and/or acute and/or chronic heart failure.

More specifically the present invention relates to the compounds of formulas (I) to (XV)

| Compound | Stucture Name | Description |
|---|---|---|
| (I) | Odanacatib | Compound according to formula (I), its production and use as pharmaceutical is described in: J. Y. Gauthier et al., Bioorg. Med. Chem. Lett. 18 (2008) 923-928; P. O'Shea et al., J. Org. Chem. (2009), 74(4), 1605-10; M. D. Truppo in: H.-U. Blaser, H.-J. Federsel (Eds.) "Asymmetric Catalysis on Industrial Scale" (2nd Edition) (2010), 397-414. |
| (II) | Balicatib | Compound according to formula (II), its production and use as pharmaceutical is described in: WO 01/58886, example 4 |
| (III) | Relacatib | Compound according to formula (III), its production and use as pharmaceutical is described in: WO 01/070232, example 5; D. S. Yamashita et al., J. Med. Chem. 2006, 49, 1597-1612 |

| Compound | Structure Name | Description |
|---|---|---|
| (IV) | 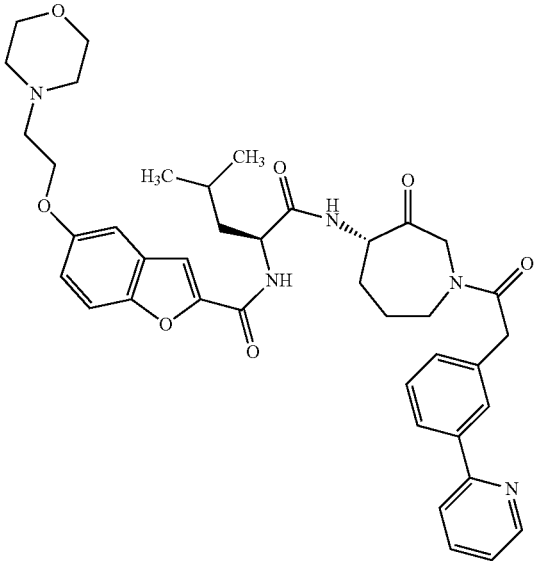<br>SB-331750 | Compound according to formula (IV), its production and use as pharmaceutical is described in: WO 00/038687 example 16;<br>R. W. Marquis et al., J. Med. Chem. 2001, 44, 1380-1395 |
| (V) | 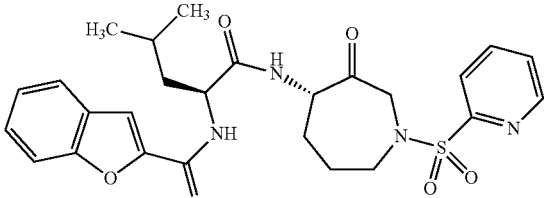<br>SB-357114 | Compound according to formula (V), its production and use as pharmaceutical is described in: WO 00/038687 example 28;<br>R. W. Marquis et al., J. Med. Chem. 2001, 44, 1380-1395 |
| (VI) | 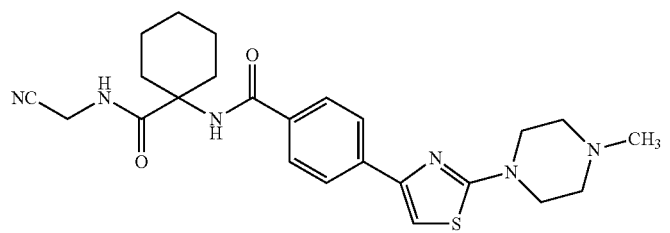<br>L-006235 | Compound according to formula (VI), its production and use as pharmaceutical is described in: WO 00/55126 example 10;<br>J. T. Palmer et al., J. Med. Chem. 2005, 48, 7520-7534 |
| (VII) | 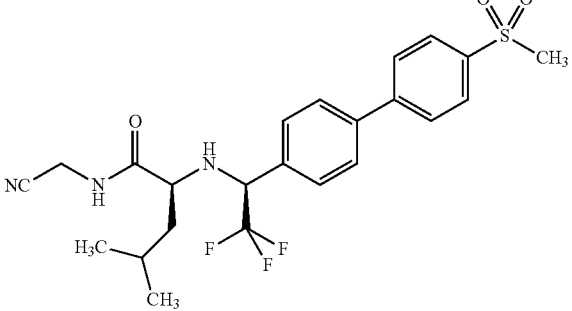<br>L-873742 | Compound according to formula (VII), its production and use as pharmaceutical is described in: WO 03/075836 example 8;<br>C. S. Li et al., Bioorg. Med. Chem. Lett. 2006, 16, 1985-1989 |

| Compound | Structure Name | Description |
|---|---|---|
| (VIII) | 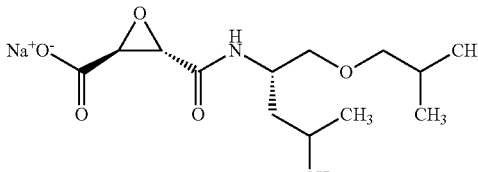<br>NC-2300 | Compound according to formula (VIII), its production and use as pharmaceutical is described in: WO 99/11640 example 48; WO 2004/096785 "Compound A" |
| (IX) | 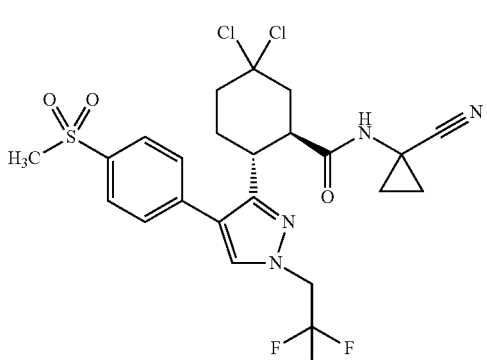<br>MK 1256 | Compound according to formula (IX), its production and use as pharmaceutical is described in: WO 2007/003056 example 2; J. Robichaud et al., J. Med. Chem. 2008, 51, 6410-6420 |

MIV 701 (X), Ono 5334 (XI), RO 4383315 (XII), SAR-114137 (XIII), MIV 710 (XIV) or MIV 711 (XV) for the use in the treatment and/or prophylaxis of pulmonary hypertension, heart failure and/or combinations thereof.

In a preferred embodiment the present invention relates to the compound of formula (I)

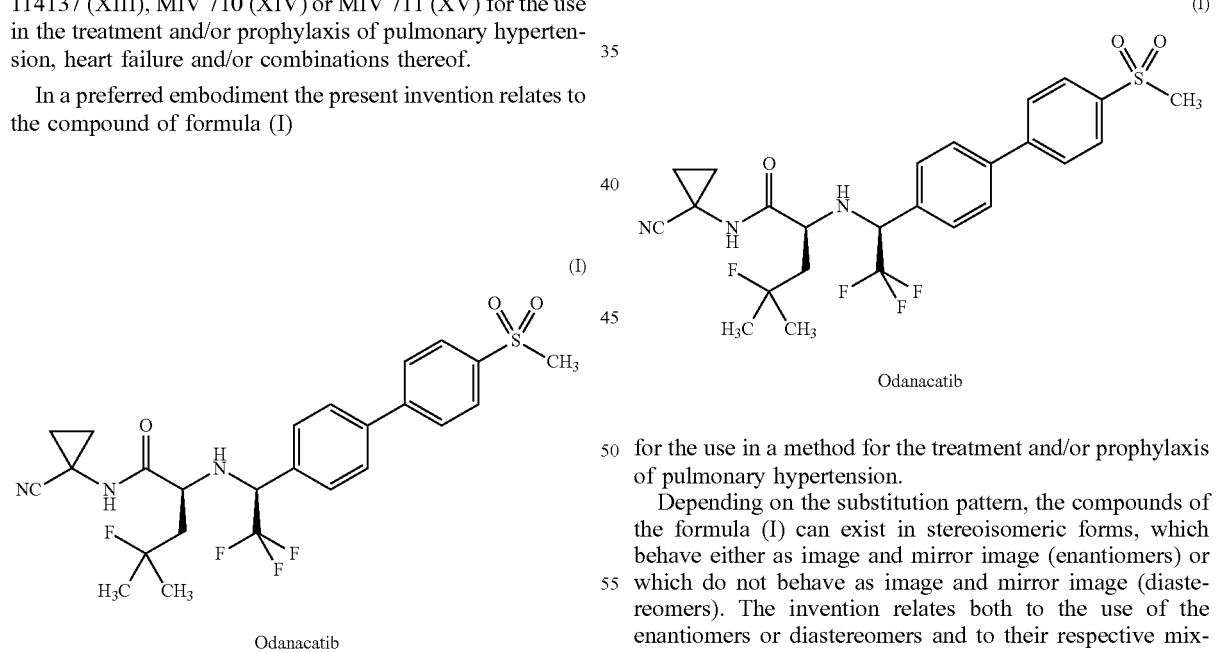

Odanacatib for the use in a method for the treatment and/or prophylaxis of pulmonary hypertension and/or acute or chronic heart failure.

In a more preferred embodiment the present invention relates to the compound of formula (I)

Odanacatib for the use in a method for the treatment and/or prophylaxis of pulmonary hypertension.

Depending on the substitution pattern, the compounds of the formula (I) can exist in stereoisomeric forms, which behave either as image and mirror image (enantiomers) or which do not behave as image and mirror image (diastereomers). The invention relates both to the use of the enantiomers or diastereomers and to their respective mixtures. Just like the diastereomers, the racemic forms can be separated into the stereoisomerically uniform constituents in a known manner. Equally, the present invention also relates to the use of the other tautomers of the compounds of the formula (I) and their salts.

Salts of the compounds of the formula (I) can be physiologically acceptable salts of the substances according to the invention with mineral acids, carboxylic acids or sulfonic acids. Particularly preferred salts are, for example, those with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, trifluoroacetic acid, acetic acid, propionic acid, lactic acid, tartaric acid, citric acid, fumaric acid, maleic acid or benzoic acid.

The compounds of the present invention appear preferably as hydrochlorides or trifluoroacetates.

Salts which can be mentioned are also salts with customary bases, such as, for example, alkali metal salts (e.g. sodium or potassium salts), alkaline earth metal salts (e.g. calcium or magnesium salts) or ammonium salts, derived from ammonia or organic amines such as, for example, diethylamine, triethylamine, ethyldiisopropylamine, procaine, dibenzylamine, N-methylmorpholine, dihydro-abietylamine, 1-ephenamine or methylpiperidine.

Hydrates or solvates are designated according to the invention as those forms of the compounds of the formula (I) which in the solid or liquid state form a molecular compound or a complex by hydration with water or coordination with solvent molecules. Examples of hydrates are sesquihydrates, monohydrates, dihydrates or trihydrates. Equally, the hydrates or solvates of salts of the compounds according to the invention are also suitable.

Animal Models

Hypoxia-Induced Pulmonary Hypertension in the Guinea Pig

Chronic hypoxia is a literature described and accepted animal model for pulmonary hypertension and is described for different species (Am J Physiol Lung Cell Mol Physiol 297: L1013-L1032, 2009; J Pharmacol Sci 107, 8-14 (2008); Pharmacology & Therapeutics 92 (2001) 1-20). Acute hypoxia increases pulmonary arterial pressure through pulmonary arterial constriction. Chronic hypoxia causes more severe pulmonary hypertension through vascular architectural changes and an increase of hematocrit (Hct) in the blood. Architectural changes include medial thickening in muscular pulmonary arteries and the appearance of new medial smooth muscle in small arteries that were previously non- or partially muscularized. This latter phenomenon is referred to as muscle extension. These changes are due to hypertrophy, hyperplasia, and distal migration of vascular smooth muscle cells or smooth muscle precursor cells such as pericytes. Thompson et al. shows those effect (including increase of right ventricular weight) in a guinea pig model (J. Appl. Physiol. 74(2): 916-921, 1993).

Pacing-Induced Heart Failure in Dogs

Experimental heart failure induced by rapid ventricular pacing in dogs results in a low output cardiomyopathic state. Myocardial remodelling and chamber dilatation occur to counteract the increased wall stress. Along with these changes there is depressed ventricular contractility. These alterations are similar to those observed in both human and naturally occurring canine dilated cardiomyopathy (DCM). Cardiomyopathies are associated with a progressive loss of myocytes throughout the ventricular wall and papillary muscles. (Cardiovascular Research 49 (2001) 127-134).

CTSK Inhibitor (Odanacatib) in Pulmonary Hypertension Guinea Pig Model

The CTSK inhibitor Odanacatib was tested in a guinea pig model for pulmonary hypertension as described in the examples section. Male Dunkin Hartley guinea pigs weighing approximately 250 g were randomized to three different treatment groups (n=7-8 animals/group; control+placebo, hypoxia+placebo, hypoxia+Odanacatib). For exposure to chronic hypoxia, the guinea pigs were kept under normobaric hypoxia (at 10% O2) in ventilated chambers for 28 days. Control animals were kept in room air. Food and water were provided ad libitum. The guinea pigs received either Odanacatib or placebo via continuous infusion by implantation of osmotic minipump from day 0 until day 28. At day 28 the animals were exsanguinated and the heart was excised. The heart was dissected, and the ratio of the right ventricle to left ventricle plus septum weight (RV/LV+S) was calculated as an index of right ventricular hypertrophy. The right ventricle was snap-frozen on dry ice for RNA extraction and quantitative real-time polymerase chain reaction. After 4 weeks of hypoxia the RV/LV+S ratio increased from 0.28±0.01 (Mean±SEM, normoxic control group) to 0.37±0.01 (Mean±SEM, hypoxic placebo group). Treatment with Odanacatib markedly and surprisingly decreased the RV/LV+S ratio to 0.30±0.01 (Mean±SEM). The results are shown in FIG. 1. Control: ratio of heart right ventricle weight vs left ventricle weight including septum under normoxia; placebo: ratio of heart right ventricle weight vs left ventricle weight including septum under hypoxia; Odanacatib: ratio of heart right ventricle weight vs left ventricle weight including septum under hypoxia and Odacatib treatment. The significant chances are marked by asterisks.

To analyse the disease state of the animals and determine the efficacy of Odanacatib treatment, the expression of marker genes were performed. The expression of ANP is increased in hearts from hypoxia kept animals, whereas Odanacatib treatment leads to a markedly decreased expression under hypoxia (compared to placebo group). The results are shown in FIG. 2. The expression of LTBP2 is increased in hearts from hypoxia kept animals, whereas Odanacatib treatment leads to a markedly decreased expression under hypoxia (compared to placebo group). The results are shown in FIG. 3. The expression of CTSK is increased in hearts from hypoxia kept animals, whereas Odanacatib treatment leads to a markedly decreased expression under hypoxia (compared to placebo group). The results are shown in FIG. 4. Due to the known correlation of increased ANP levels and disease stage in heart failure patients and animal models, the increased expression of CTSK seems to be correlated with pulmonary hypertension. The treatment of hypoxia-induced pulmonary hypertension animals with Odanacatib leads to a reduction of right ventricle weight compared to placebo treated animals. Here we show that Odanacatib and other in the invention presented CTSK inhibitors are useful to treat pulmonary hypertension.

The nucleotide sequence of a guinea pig CTSK is identified as SEQ ID NO:1.

The polypeptide sequence of a guinea pig CTSK is identified as SEQ ID NO:2.

CTSK Expression in Pacing-Induced Heart Failure in Dogs

The expression of CTSK in heart samples from pacing-induced heart failure dogs were performed to analyse the relevance of CTSK in heart failure. The experiment was performed as described in the example section (example animal models A-4).

The expression analysis of ANP and CTSK were performed as described in the example section for left atrium, right atrium, left ventricle and right ventricle. The results are shown in FIG. 5 for the expression of CTSK and in FIG. 6 for ANP. The expression of CTSK is increased in left atrium, right atrium, left ventricle and right ventricle of paced dogs compared to tissues from unpaced dogs. The expression of ANP is increased in right and left atria from paced dogs compared to tissues from unpaced dogs. Due to the known correlation of increased ANP levels and disease stage in heart failure patients and animal models, the increased expression of CTSK seems to be correlated with heart failure. Here we show that CTSK expression is upregulated in heart failure and that the inhibition of CTSK by inhibitors (presented in the invention) like, but not limited to Odanacatib is useful for the treatment of heart failure.

Indications

Acute hypoxia elicits strong pulmonary arterial vasoconstriction and increases the pulmonary artery pressure [5]. This so-called Euler-Liljestrand mechanism describes the connection between ventilation and blood circulation (perfusion) of the lung and is also known as hypoxic pulmonary vasoconstriction [6]. Chronic hypoxia results in extensive vascular remodeling, pulmonary hypertension, and cor pulmonale [7]. The vascular remodeling process mainly affects the distal braches of the pulmonary arteries: both vascular smooth muscle cells (VSMCs) and adventitial fibroblasts proliferate under these conditions [8].

Pulmonary hypertension (Clinical Classification of Pulmonary Hypertension, Dana Point 2008) is a progressive lung disorder which may have various causes and, untreated, results in death. It is associated with an overload on the right heart with right heart failure progressing to pump failure, which may result in death. By definition, in chronic pulmonary hypertension the mean pulmonary artery pressure (mPAP) is >25 mmHg at rest and >30 mmHg during exercise (normal value <20 mmHg). Both pulmonary arterial vasoconstriction and structural remodeling of the pulmonary vessels are integral features of the pathological processes contributing to an elevated pulmonary pressure in this disease. The remodeling is characterized by neomuscularization, medial hypertrophy and adventitial thickening. This increasing obliteration of the pulmonary circulation results in a progressive stress on the right heart, leading to a reduced output by the right heart and finally terminating in right heart failure.

So called idiopathic pulmonary arterial hypertension (PAH), which occurs without identifiable cause, is an extremely rare disorder with a prevalence of 1-2 per million [3]. The average age of the patients has been estimated to be 36 years, and only 10% of the patients were over 60 years of age. Distinctly more women than men are affected. The secondary forms of pulmonary hypertension show, consistent with the diversity of the causes underlying them, different courses, but in every case it is a severe disorder with high mortality.

Despite all the advances in the therapy of pulmonary hypertension, there is as yet no prospect of curing this serious disorder. Specific therapies available on the market for pulmonary hypertension (e.g. prostacyclin analogues, endothelin receptor antagonists, phosphodiesterase inhibitors) are, however, able to improve the quality of life, the exercise tolerance and the prognosis of the patients. However, the usability of these medicaments is restricted by the in some cases serious side effects and/or complicated administration forms. The period over which the patients' clinical situation can be improved or stabilized with a specific therapy is limited. Eventually, the therapy escalates and thus a combination therapy is applied, where a plurality of medicaments must be given concurrently. Novel combination therapies are one of the most promising future therapeutic options for the treatment of pulmonary arterial hypertension [4]. It is increasingly important in the development of novel therapies for them to be combinable with known ones and not generate any problems associated with metabolism, e.g. inhibit P450 CYP enzymes to only a very small extent or not at all (compare medicament interactions associated with combination therapy with bosentan and warfarin).

The term "pulmonary hypertension" includes particular forms of pulmonary hypertension as specified by the Clinical Classification of Pulmonary Hypertension, Dana Point 2008. Examples which may be mentioned are pulmonary arterial hypertension, pulmonary hypertension associated with left heart disorders, pulmonary hypertension associated with lung disease and/or hypoxia, pulmonary hypertension due to chronic thromboembolisms (CTEPH) and/or pulmonary hypertension with unclear multifactorial mechanisms.

"Pulmonary arterial hypertension" includes idiopathic pulmonary arterial hypertension (IPAH, formerly also referred to as primary pulmonary hypertension), heritable pulmonary arterial hypertension, drug- and toxin-induced pulmonary arterial hypertension and associated pulmonary arterial hypertension (APAH) which is associated with connective tissue diseases, congenital heart diseases, portal hypertension, HIV infections, Schistosomiasis, chronic haemolytic anemia, with disorders with significant venous/capillary involvement such as pulmonary venoocclusive disease and pulmonary capillary haemangiomatosis, and/or persistent pulmonary hypertension of newborns.

Pulmonary hypertension associated with left heart disorders includes disorders with systolic dysfunction, diastolic dysfunction and valvular diseases. Pulmonary hypertension associated with lung disease and/or hypoxia includes chronic obstructive pulmonary disorders, interstitial lung disease, other pulmonary diseases with mixed restrictive and obstructive pattern, sleep apnoea syndrome, alveolar hypoventilation, chronic altitude sickness and constitutional abnormalities. Pulmonary hypertension due to chronic thromboembolisms (CTEPH) includes thromboembolic obstruction of proximal pulmonary arteries, thromboembolic obstruction of distal pulmonary arteries and/or non-thrombotic pulmonary embolisms (tumour, parasites, foreign bodies).

Pulmonary hypertension with unclear multifactorial mechanisms includes hematologic disorders (myeloproliferative disorders, splenectomy), systemic disorders (sarcoidosis, pulmonary Langerhans cell histiocytosis, lymphangioleiomyomatosis, neurofibromatosis, vasculitis), metabolic disorders (thyroid disorders, glycogen storage diseases, Gaucher's disease) and/or other disorders like tumoral obstruction, fibrosing mediastinitis, chronic renal failure on dialysis.

The term "heart failure" includes particular forms of heart failure. Examples which may be mentioned are acute decompensated heart failure, right heart failure, left heart failure, biventricular failure, ischemic cardiomyopathy, dilated cardiomyopathy, hypertrophic cardiomyopathy, idiopathic cardiomyopathy, congenital heart diseases, diastolic heart failure, systolic heart failure, congestive heart failure, and/or heart failure associated with valvular diseases, mitral valve stenosis, mitral insufficiency, aortic valve stenosis, aortic insufficiency, tricuspid valve stenosis, tricuspid insufficiency, pulmonary valve stenosis, pulmonary insufficiency, combined valvular diseases, myocarditis, acute myocarditis, chronic myocarditis, viral myocarditis, diabetis, the abuse of drugs such as alcohol and cocaine, pharmaceutical drugs such as chemotherapeutic agents, connective tissue diseases, HIV and storage diseases.

Combination Therapies

The present invention further relates to medicaments comprising a compound according to the invention and one or more further active ingredients, especially for the treatment and/or prophylaxis of the aforementioned disorders. Examples of suitable combination active ingredients which may preferably be mentioned are:

lipid-lowering agents, especially HMG-CoA (3-hydroxy-3-methylglutarylcoenzyme A) reductase inhibitors;

coronary therapeutics/vasodilators, especially ACE (angiotensin converting enzyme) inhibitors, AII (angiotensin II) receptor antagonists; □-adrenoceptor antagonists; alpha-1 adrenoceptor antagonists; diuretics; calcium channel blockers; endothelin receptor antagonists, mineralocorticoid-receptor antagonists, renninhibitors, rho-kinase-inhibitors and substances which bring about an increase in cyclic guanosine monophosphate (cGMP), such as, for example, stimulators or activators of soluble guanylate cyclase;

plasminogen activators (thrombolytics/fibrinolytics) and compounds which increase thrombolysis/fibrinolysis, such as inhibitors of plasminogen activator inhibitor (PAI inhibitors), inhibitors of the thrombin-activated fibrinolysis inhibitor (TAFI inhibitors) and factor Xa inhibitors;

substances having anticoagulant activity (anticoagulants);

platelet aggregation-inhibiting substances (platelet aggregation inhibitors);

fibrinogen receptor antagonists (glycoprotein IIb/IIIa antagonists);

antiarrhythmics;

kinase inhibitors;

stimulators and activators of soluble guanylate cyclase;

prostacyclin analogues;

endothelin receptor antagonists;

elastase inhibitors and phosphodiesterase inhibitors matrix metalloproteinase-inhibitors serotonin-receptor antagonists diuretics organic nitrates and NO-donors positive inotropic agents, for example, digitales glycosides (digoxin), dopamine, dobutamine and dopaminergic agonists, beta adrenergic agonists, adrenaline, noradrenaline natriuretic peptides Calcium sensitizer, for example levosimendan CTSS inhibitors Bronchodilators, for example albuterol, metaproterenol, terbutaline, salmeterol, formoterol, bambuterol Anti-iflammatory drugs, for example glucocorticoids.

The present invention further relates to a method for the treatment and/or prophylaxis of pulmonary hypertension in humans and animals by administering an effective amount of at least one selective cathepsin K inhibitor of the formulas (I) to (XV) or of a medicament comprising at least one selective cathepsin K inhibitor in combination with an inert, non-toxic, pharmaceutically suitable excipient.

The present invention further relates to a method for the treatment and/or prophylaxis of pulmonary hypertension in humans and animals through administration of an effective amount of compound of formula (I), or of a medicament comprising at least one compound of the invention, in combination with an inert, non-toxic, pharmaceutically suitable excipient.

The medicaments to be manufactured in accordance with the use according to the invention or to be used according to the invention comprise at least one compound of the invention, normally together with one or more inert, non-toxic, pharmaceutically suitable excipients.

The compounds according to the invention can act systemically and/or locally. For this purpose, they can be administered in a suitable way such as, for example, by the oral, parenteral, pulmonary, nasal, sublingual, lingual, buccal, rectal, dermal, transdermal, conjunctival or otic route or as implant or stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Suitable for the other administration routes are, for example, pharmaceutical forms for inhalation (inter alia powder inhalers, nebulizers), nasal drops, solutions or sprays, tablets, films/wafers or capsules to be administered by the lingual, sublingual or buccal route, suppositories, preparations for the eyes or ears, vaginal capsules, aqueous suspensions (lotions, shaking mixtures), lipophilic suspensions, ointments, creams, transdermal therapeutic systems (e.g. patches), milk, pastes, foams, dusting powders, implants or stents.

In a more preferred embodiment the present invention relates to the aforementioned compounds or pharmaceutical compositions/medicaments for the use in a method for the treatment and/or prophylaxis of a disease comprised in a group of diseases consisting of pulmonary arterial hypertension, pulmonary hypertension associated with left heart disorders, pulmonary hypertension associated with lung disease and/or hypoxia, and pulmonary hypertension due to chronic thromboembolisms (CTEPH). An even more preferred embodiment is the use in a method for the treatment and/or prophylaxis of pulmonary arterial hypertension.

In a more preferred embodiment the present invention relates to the aforementioned compounds or pharmaceutical compositions/medicaments for the use in a method for the treatment and/or prophylaxis of chronic heart failure.

In a more preferred embodiment the present invention relates to the aforementioned compounds or pharmaceutical compositions/medicaments for the use in a method for the treatment and/or prophylaxis of dilated cardiomyopathy.

Diagnostics

In another embodiment, antibodies which specifically bind CTSK may be used for the diagnosis of pulmonary hypertension or heart failure, or in assays to monitor patients being treated with CTSK inhibitors. Antibodies useful for diagnostic purposes may be prepared in the same manner as those described above for therapeutics. Diagnostic assays for CTSK include methods which utilize the antibody and a label to detect CTSK in human body fluids or in extracts of cells or tissues, preferably in heart tissue, more preferred in heart ventricle (left and/or right) and even more preferred in right ventricle. The antibodies may be used with or without modification, and may be labeled by covalent or non-covalent joining with a reporter molecule.

A variety of protocols for measuring CTSK, including ELISAs, RIAs, and FACS, are known in the art and provide a basis for diagnosing altered or abnormal levels of CTSK expression. Normal or standard values for CTSK expression are established by combining body fluids or cell extracts taken from normal mammalian subjects, preferably human, with antibody to CTSK under conditions suitable for complex formation The amount of standard complex formation may be quantified by various methods, preferably by photometric means. Quantities of CTSK expressed in subject samples from biopsied tissues are compared with the standard values. Deviation between standard and subject values establishes the parameters for diagnosing disease.

In another embodiment of the invention, the polynucleotides encoding CTSK may be used for diagnostic purposes. The polynucleotides which may be used include oligonucleotide sequences, complementary RNA and DNA molecules, and PNAs. The polynucleotides are used to detect and quantitate gene expression in biopsied tissues preferably of the aforementioned heart samples in which expression of CTSK correlates with disease. The diagnostic assay may be used to distinguish between absence, presence, and excess expression of CTSK, and to monitor regulation of CTSK levels during therapeutic intervention.

Polynucleotide sequences encoding CTSK may be used for the diagnosis of disorders of the peripheral and central nervous system, hematology diseases, cancer diseases and cardiovascular diseases associated with expression of CTSK. The polynucleotide sequences encoding CTSK may be used in Southern, Northern, or dot-blot analysis, or other membrane-based technologies; in PCR technologies; in dipstick, pin, and ELISA assays; and in microarrays utilizing fluids or tissues from patient biopsies to detect altered CTSK expression. Such qualitative or quantitative methods are well known in the art.

In a particular aspect, the nucleotide sequences encoding CTSK may be useful in assays diagnosing pulmonary hypertension or heart failure. The nucleotide sequences encoding CTSK may be labelled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered from that of a comparable control sample, the nucleotide sequences have hybridized with nucleotide sequences in the sample, and the presence of altered levels of nucleotide sequences encoding CTSK in the sample indicates the presence of the associated disorder. Such assays may also be used to evaluate the efficacy of a particular therapeutic treatment regimen in animal studies, in clinical trials, or in monitoring the treatment of an individual patient.

In order to provide a basis for the diagnosis of pulmonary hypertension or heart failure, a normal or standard profile for expression is established. This may be accomplished by combining body fluids or cell extracts taken from normal subjects, either animal or human, with a sequence, or a fragment thereof, encoding CTSK, under conditions suitable for hybridization or amplification. Standard hybridization may be quantified by comparing the values obtained from normal subjects with values from an experiment in which a known amount of a substantially purified polynucleotide is used. Standard values obtained from normal samples may be compared with values obtained from samples from patients who are symptomatic for a disorder. Increased values compared to standard values diagnose the presence of an aforementioned disorder.

Another object of the invention is a method of diagnosing a disease comprised in a group of diseases consisting of pulmonary hypertension, of pulmonary arterial hypertension, pulmonary hypertension associated with left heart disorders, pulmonary hypertension associated with lung disease and/or hypoxia, pulmonary hypertension due to chronic thromboembolisms (CTEPH) and heart failure in a mammal comprising the steps of (i) determining the amount of a CTSK polynucleotide or polypeptide in a sample taken from said mammal, (ii) determining the amount of CTSK polynucleotide or polypeptide in healthy and/or diseased mammal. A preferred embodiment is the diagnosis of pulmonary arterial hypertension or chronic or acute heart failure. A disease is diagnosed, if there is a substantial similarity in the amount of CTSK polynucleotide or polypeptide in said test mammal as compared to a diseased mammal. A disease is diagnosed, if the amount of CTSK polynucleotide or polypeptide in said test mammal is increased compared to a healthy mammal. In a preferred embodiment the amount of CTSK polynucleotide or polypeptide is increased at least 1.5 fold.

Primers

The following primers can be used in the animal models described above:

Nucleotide sequence of primers for guinea pig CTSK: SEQ ID NO:3, SEQ ID NO:4, and SEQ ID NO:5

Nucleotide sequence of primers for guninea pig ANP: SEQ ID NO:6, SEQ ID NO:7, and SEQ ID NO:8

Nucleotide sequence of primers for guninea pig LTBP2: SEQ ID NO:9, SEQ ID NO:10, and SEQ ID NO:11

Nucleotide sequence of primers for guninea pig b-actin: SEQ ID NO:12, SEQ ID NO:13, and SEQ ID NO:14

Nucleotide sequence of primers for dog L32: SEQ ID NO:15, SEQ ID NO:16, and SEQ ID NO:17.

Nucleotide sequences of primers for dog CTSK: SEQ ID NO:18, SEQ ID NO:19, and SEQ ID NO:20.

Nucleotide sequence of primers for dog ANP: SEQ ID NO:21, SEQ ID NO:22, and SEQ ID NO:23.

A: Experimental Methods

A-1. Example 1

Expression Analysis

Guinea pig or dog tissues were pulverized by grinding with liquid nitrogen. Total RNA was extracted, DNase I digestion was performed to remove residual genomic DNA and the RNA were reverse transcribed using random hexomer primers. Quantitative TaqMan RT-PCR analysis was performed using the Applied Biosystems PRISM 7900 sequence detection system. The thermal protocol was set to 2 min at 50° C., followed by 10 min at 95° C. and by 40 cycles of 15 s at 95° C. and 1 min at 60° C. Results were normalized to L32 (dog) or b-actin (guinea pig) controls, and relative expression was calculated according to the following formula: relative expression=$2(20-(CT(probe)-CT(L32/b-actin)))$. The parameter CT is defined as the cycle number at which the amplification plot passes a fixed threshold above baseline.

A-2. Example 2

Use of LTBP2 as a Biomarker, therapeutic and diagnostic Target in cardiovascular disease (hypoxia-induced pulmonary hypertension)

The hypoxia-induced pulmonary hypertension model is described in the section animal model (A-3.)

Total cellular RNA was isolated with the Trizol-Reagent protocol according to the manufacturer's specifications (Invitrogen; USA). Total RNA prepared by the Trizol-reagent protocol was treated with DNAse I to remove genomic DNA contamination.

For relative quantitation of the mRNA distribution of LTBP2, total RNA from each sample was first reverse transcribed. 1 µg of total RNA was reverse transcribed using ImProm-II Reverse Trascription System (Promega, USA) according to the manufactures protocol. The final volume was adjusted to 200 µl with water.

For relative quantitation of the distribution of LTBP2 mRNA the Applied Bioscience ABI 7900HT Sequence Detection system was used according to the manufacturer's specifications and protocols.

PCR reactions were set up to quantitate LTBP2 and the housekeeping gene b-actin. Forward and reverse primers and probes for LTBP2 were designed using the Applied Bioscience ABI Primer Express™ software and were synthesized by Eurogentec (Belgium). The LTBP2 forward primer sequence was: Primer1 (SEQ ID NO: 9). The LTBP2 reverse primer sequence was Primer2 (SEQ ID NO: 10). Probe1 (SEQ ID NO: 11), labelled with FAM (carboxyfluorescein succinimidyl ester) as the reporter dye and TAMRA (carboxytetramethylrhodamine) as the quencher, is used as a probe for LTBP2. The following reagents were prepared in a total of 20 µl:1x qPCR-MasterMix (Eurogentec; Belgium) and Probe1 (SEQ ID NO: 11), LTBP2 forward and reverse primers each at 200 nM, 200 nM LTBP2 FAM/TAMRA-labelled probe, and 5 µl of template cDNA. Thermal cycling parameters were 2 min at 50° C., followed by 10 min at 95° C., followed by 40 cycles of melting at 95° C. for 15 sec and annealing/extending at 60° C. for 1 min.

Calculation of Relative Expression

The CT (threshold cycle) value is calculated as described in the "Quantitative determination of nucleic acids" section.

$$deltaCT = CT LTBP2 - CT b\text{-actin}$$

$$relative\ expression = 2^{(15-deltaCT)}$$

The results of the mRNA-quantification (expression profiling) is shown in FIG. 3.

Animal Models

Advantageous pharmacological properties of the compounds which can be used according to the invention can be ascertained by the following methods.

A-3. Animal Model of Hypoxia-Induced Pulmonary Hypertension in the Guinea Pig Treatment with CTSK Inhibitors Male Dunkin Hartley guinea pigs weighing approximately 250 g were randomized to three different treatment groups (n=7-8 animals/group; control+placebo, hypoxia+placebo, hypoxia+Odanacatib). For exposure to chronic hypoxia, the guinea pigs were kept under normobaric hypoxia (at 10% $O_2$) in ventilated chambers for 28 days. Control animals were kept in room air. Food and water were provided ad libitum. The guinea pigs received either Odanacatib or placebo via continuous infusion by implantation of osmotic minipump from day 0 until day 28. At day 28 the animals were exsanguinated and the heart was excised. The heart was dissected, and the ratio of the right ventricle to left ventricle plus septum weight (RV/LV+S) was calculated as an index of right ventricular hypertrophy. The right ventricle was snap-frozen on dry ice for RNA extraction and quantitative real-time polymerase chain reaction. After 4 weeks of hypoxia the RV/LV+S ratio increased from 0.28±0.01 (Mean±SEM, normoxic control group) to 0.37±0.01 (Mean±SEM, hypoxic placebo group). Treatment with Odanacatib markedly decreased the RV/LV+S ratio to 0.30±0.01 (Mean±SEM). The results are shown in FIG. 1. Control: ratio of heart right ventricle weight vs left ventricle weight including septum under normoxia; placebo: ratio of heart right ventricle weight vs left ventricle weight including septum under hypoxia and placebo infusion; Odanacatib: ratio of heart right ventricle weight vs left ventricle weight including septum under hypoxia and Odacatib treatment. The significance is marked by an asterisk.

A-4. Paced Dog

The acute experimental setup is summarized in FIG. 7. For pacemaker implantation (day 0) and hemodynamic evaluation (day 21) mongrel dogs (Marshall BioResources/USA) weighting between 25 and 32 kg were anesthetized with pentobarbital (15 to 30 mg/kg to effect). Anesthesia supplementation was provided by pentobarbital (1-5 mg/kg/h) used as needed and administered through the left cephalic vein. For analgesia, fentanyl (10-40 µg/kg/h) was infused through the right cephalic vein. During all experimental procedures animals were intubated and mechanically ventilated with room air using a Sulla 808 anesthesia ventilator (Drager/Germany).

Pacemaker Implantation

Under fluoroscopic guidance (OEC FlexiView 8800, GE Healthcare/USA) and under sterile conditions a steroid-eluting pacemaker lead (Setrox S60, Biotronik/Germany) was inserted through an axillary vein into the right ventricle and connected to a pacemaker (Logos, Biotronik/Germany). To confirm the correct placement, capture threshold and intracardiac signal were measured. All animals received parenteral antibiotic (Enrofloxacin (Baytril®), Bayer/Germany; 5 mg/kg; s.c.) and analgesic (Metamizole (Metamizole-WDT®) WDT/Germany; 50 mg/kg; i.m.) treatment over a period of 3 days after pacemaker implantation. Following wound healing (day 7) the pacemaker was activated and the heart paced continuously at a rate of 220 beats per minute (BPM) for 14 days. During this pacing period dogs were kept in a stable, access to food and water was provided ad lib and dogs were allowed into a play area twice daily. The dogs were observed and clinically evaluated daily for the duration of the study.

Acute Experimental Setup

After 14 days of pacing the animals were studied under general anesthesia to evaluate their hemodynamic and urine output response to intravenous Conivaptan- (0.1 mg/kg i.v.) or Tolvaptan-bolus (0.1 mg/kg i.v.), respectively. On the day of the study, the pacemaker was disabled one hour before induction of anesthesia. Under sterile conditions the animals were instrumented with femoral artery access (to measure arterial blood pressure via NaCl 0.9% filled sheath introducer (Cordis, Waterloo/Belgium) and LV performance (rate, contractility as well as relaxation) was assessed using ECG and a 5F-microtip catheter (Millar Instruments Inc., Houston/USA)). Through an axillary vein a Swan Ganz catheter (CCOmbo with Vigilance-monitor, Edwards Lifescience/USA) was introduced to measure cardiac output, pulmonary artery pressure, central venous pressure and body temperature. All data were recorded with a Gould Amplifier and ACQ-16 Acquisition Interface Unit and further analyzed with the Ponemah software (all DSI/St. Paul/USA). A urinary bladder catheter was inserted and urine output was measured every 20 minutes. The physiological effects are described in Mondritzki et al. (Am J. Ther. 2010 Dec 29.)

A-5. Biomarkers

Classes:
Disease Biomarker: a biomarker that relates to a clinical outcome or measure of disease.
Efficacy Biomarker: a biomarker that reflects beneficial effect of a given treatment.
Staging Biomarker: a biomarker that distinguishes between different stages of a chronic disorder.
Surrogate Biomarker: a biomarker that is regarded as a valid substitute for a clinical outcomes measure.
Toxicity Biomarker: a biomarker that reports a toxicological effect of a drug on an in vitro or in vivo system.
Mechanism Biomarker: a biomarker that reports a downstream effect of a drug.
Target Biomarker: a biomarker that reports interaction of the drug with its target.

ANP

Atrial natriuretic peptide (ANP), atrial natriuretic factor (ANF), atrial natriuretic hormone (ANH), or atriopeptin, is a powerful vasodilator, and a protein (polypeptide) hormone secreted by heart muscle cells.[11]. It is involved in the homeostatic control of body water, sodium, potassium and fat (adipose tissue). It is released by muscle cells in the upper chambers (atria) of the heart (atrial myocytes), in response to high blood pressure. ANP acts to reduce the water, sodium and adipose loads on the circulatory system, thereby reducing blood pressure. ANP binds to a specific set of receptors—ANP receptors. Receptor-agonist binding causes a reduction in blood volume and therefore a reduction in cardiac output and systemic blood pressure. Lipolysis is increased and renal sodium reabsorption is decreased. The overall effect of ANP on the body is to counter increases in blood pressure and volume caused by the renin-angiotensin system.

ANP is a well known disease biomarker, staging biomarker, surrogate biomarker efficacy biomarker for pulmonary hypertension (Pflugers Arch. 1997 May; 434(1):63-9.; Clin Chim Acta. 2000 November; 301(1-2):19-30.; Chest. 2004 October; 126(4):1330-6.) and heart failure (Clin. Cardiol. 33, 11, 700-707 (2010)).

Renal:

Dilates the afferent glomerular arteriole, constricts the efferent glomerular arteriole, and relaxes the mesangial cells. This increases pressure in the glomerular capillaries, thus increasing the glomerular filtration rate (GFR), resulting in greater excretion of sodium and water. Increases blood flow through the vasa recta which will wash the solutes (NaCl and urea) out of the medullary interstitium. [6] The lower osmolarity of the medullary interstitum leads to less reabsorption of tubular fluid and increased excretion. Decreases sodium reabsorption in the proximal convoluted tubule and cortical collecting duct of the nephron via guanosine 3',5'-cyclic monophosphate (cGMP) dependent phosphorylation of ENaC. Inhibits renin secretion, thereby inhibiting the renin-angiotensin system. Reduces aldosterone secretion by the adrenal cortex.

Vascular:

Relaxes vascular smooth muscle in arterioles and venules by: Membrane Receptor-mediated elevation of vascular smooth muscle cGMP Inhibition of the effects of catecholamines Cardiac:

Inhibits maladaptive cardiac hypertrophy. Mice lacking cardiac NPRA develop increased cardiac mass and severe fibrosis and die suddenly. Re-expression of NPRA rescues the phenotype. It may be associated with isolated atrial amyloidosis.

LTBP2

The nucleotide sequence of LTBP2 is accessible in the databases by the accession number Z37976 (human). The primer sequences are given in SEQ ID NO:9-11 (guinea pig)

The transforming growth factor beta (TGFβ) cytokines are a multifunctional family that exert a wide variety of effects on both normal and transformed mammalian cells. The secretion and activation of TGFβ s is regulated by their association with latency associated proteins and latent TGFβ binding proteins (LTBPs). Transforming growth factor β (TGFβ) exists as three mammalian isoforms (TGFβ1, TGFβ2 and TGFβ3). Each of these is usually secreted in large latent complexes (LLCs) which have no biological activity and comprise three components: a disulphide bonded homodimer of mature TGFβ associated non-covalently with latentcy-associated proteins (LAPs; homodimers of the N-terminal fragment of precursor TGFβ) and a covalently attached molecule of latent TGFβ binding protein (LTBP) Four LTBP genes have been identifed: LTBP1 to LTBP4. LAPs are sufficient to render the mature homodimer inactive, and removal of both the LAPs and LTBP or modulation of their interaction is essential for any of the TGFβ isoforms to function. The TGFβ cytokines modulate the growth and functions of a wide variety of mammalian cell types. It has become evident in recent years that LTBPs may be involved in the assembly, secretion and targeting of TGFβ to sites at which it is stored and/or activated. Thus these proteins may play critical roles in controlling and directing the activity of TGFβs. LTBPs may also exert effects independently of those associated with TGFβ, for example as structural matrix proteins.

Relatively little is known about the functional role of LTBP2. Unlike the other LTBPs, LTBP2 is unable to associate with the small latent □□ TGFβ. LTBP2 is expressed mostly in the lung and to a lesser extent in the liver, skeletal muscle placenta and heart. □Latent TGFβ binding protein LTBP2 decreases fibroblast adhesion to fibronectin. Elucidation of the functional role of LTBP2 is further limited by the fact that deletion of LTBP2 in mice leads to embryonic lethality.

Regarding a functional role of LTBP2 in the cardiovascular system, it was demonstrated that LTBP2 synthesis increased in response to arterial injury in a porcine model of coronary angioplasty [9]. Thus, together with the well known role of TGFβ in the developing of heart failure [10] our finding that TGFβ-function modifying LTBP2 is regulated on RNA level in LVAD hearts as well as in various animal models of heart failure makes LTBP2 an attractive candidate biomarker for CHF.

LTBP2 is published (but not limited to) in patents WO 2004/075835 and WO 02/068579.

REFERENCES

Figure 1:
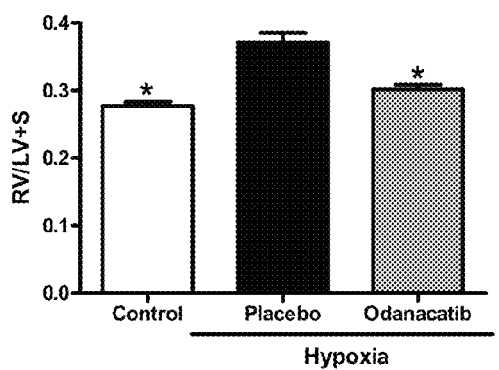
FIG. 1 shows heart weight of hypoxia-induced pulmonary hypertension model in guinea pig. Control: ratio of heart right ventricle weight vs. left ventricle weight including septum under normoxia; placebo: ratio of heart right ventricle weight vs. left ventricle weight including septum under hypoxia and placebo infusion; Odanacatib: ratio of heart right ventricle weight vs. left ventricle weight including septum under hypoxia and Odacatib treatment.
Figure 2:
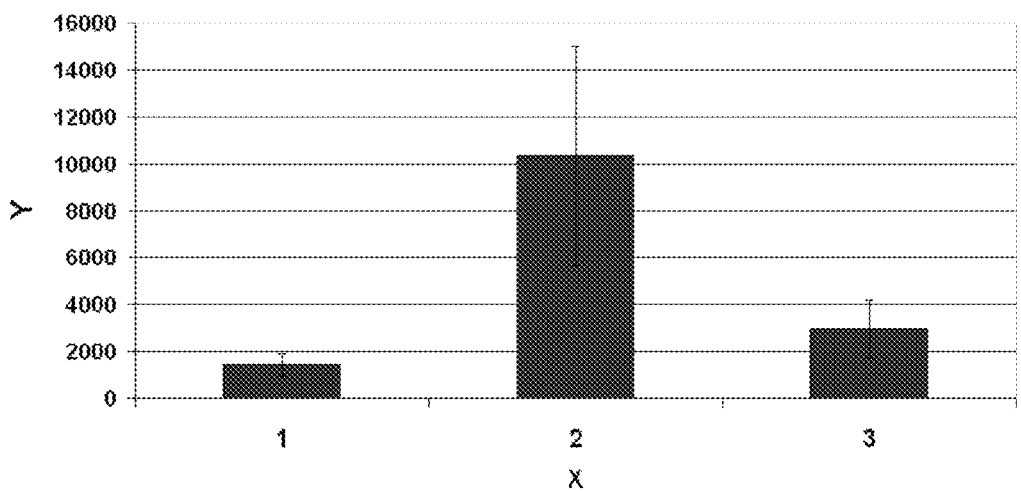
FIG. 2 shows relative expression of ANP in heart right ventricle of hypoxia-induced pulmonary hypertension model in guinea pig (X axis: 1=control, 2: placebo, 3: Odanacatib; Y axis: relative expression). Control: animals kept under normoxia; placebo: animals kept under hypoxia and placebo infusion; Odanacatib: animals kept under hypoxia and Odanacatib infusion.
Figure 3:
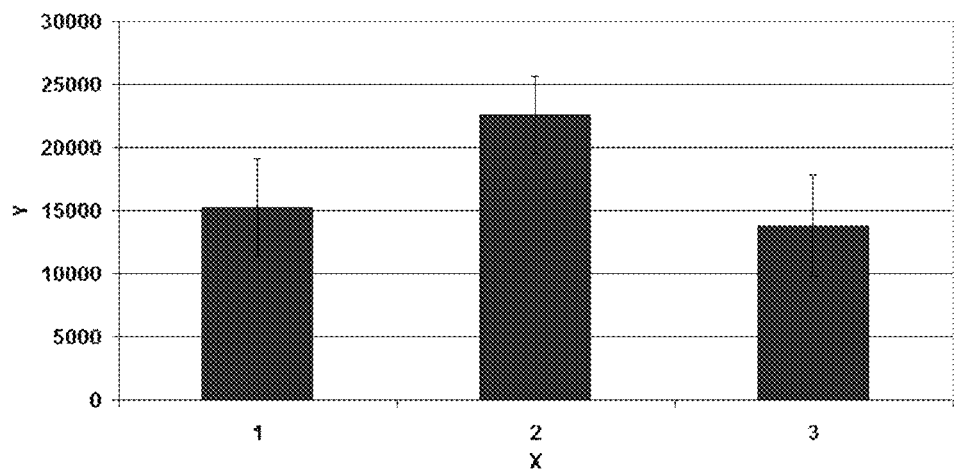
FIG. 3 shows relative expression of LTBP2 in heart right ventricle of hypoxia-induced pulmonary hypertension model in guinea pig (X axis: 1=control, 2: placebo, 3: Odanacatib; Y axis: relative expression). Control: animals kept under normoxia; placebo: animals kept under hypoxia and placebo infusion; Odanacatib: animals kept under hypoxia and Odanacatib infusion.
Figure 4:
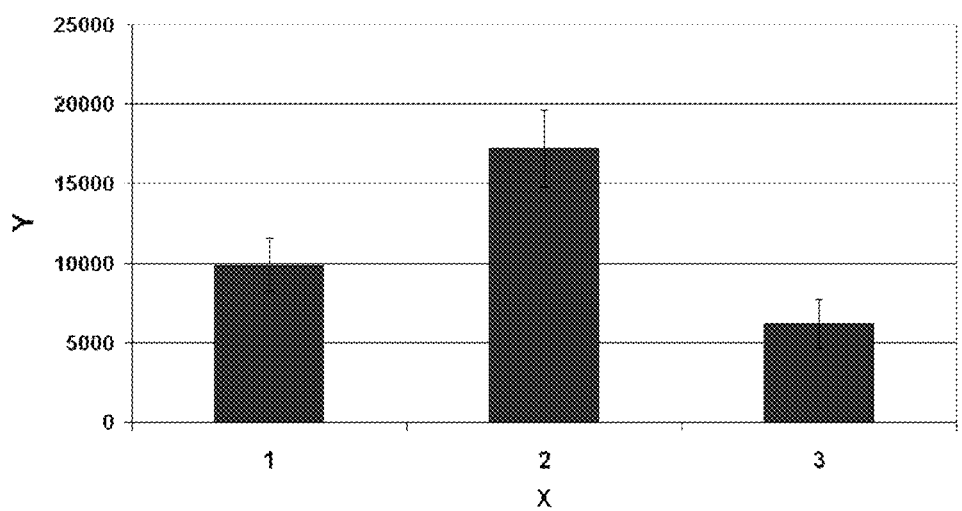
FIG. 4 shows relative expression of CTSK in heart right ventricle of hypoxia-induced pulmonary hypertension model in guinea pig (X axis: 1=control, 2: placebo, 3: Odanacatib; Y axis: relative expression). Control: animals kept under normoxia; placebo: animals kept under hypoxia and placebo infusion; Odanacatib: animals kept under hypoxia and Odanacatib infusion.
Figure 5:
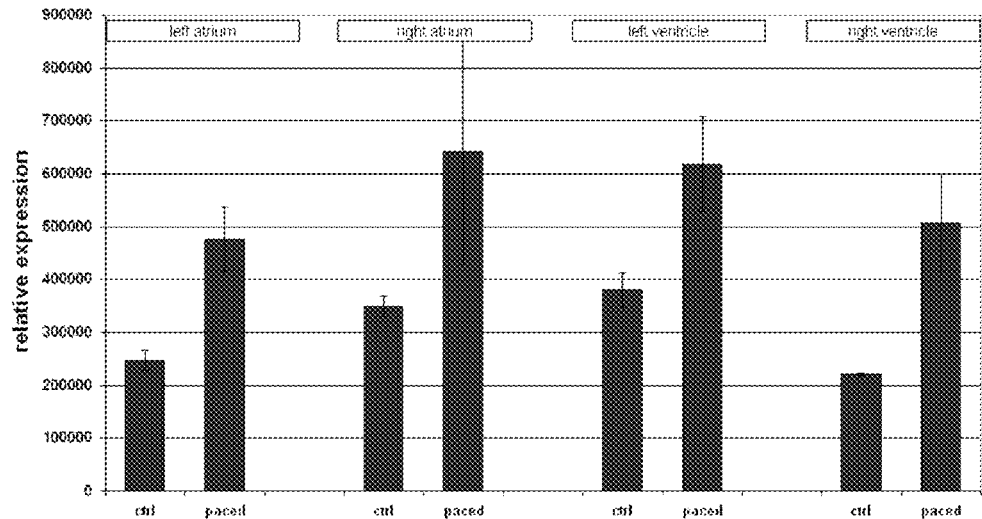
FIG. 5 shows relative expression of CTSK in heart right ventricle, left ventricle, right atrium and left atrium samples of a dog heart failure model. Control: animal without pacing; paced: animal with pacing.
Figure 6:
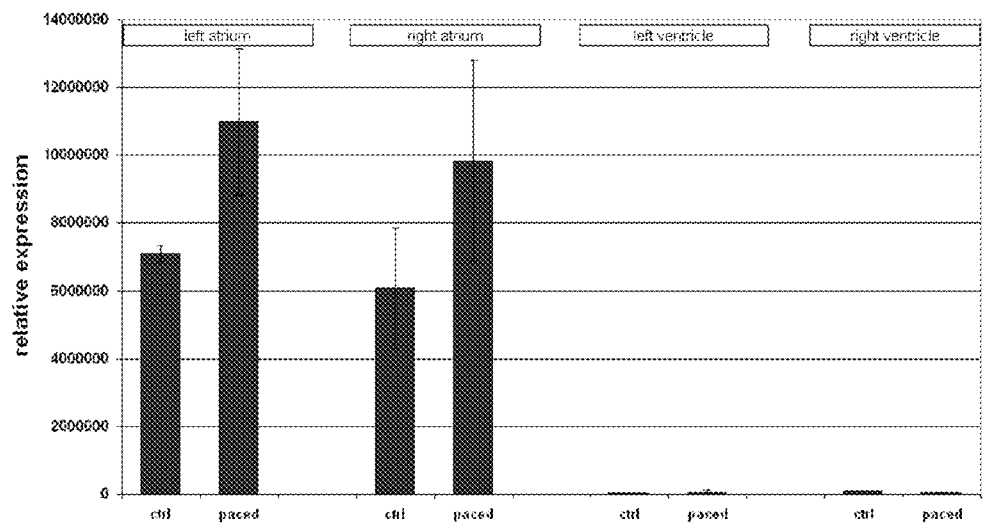
FIG. 6 shows relative expression of ANP in heart right ventricle, left ventricle, right atrium and left atrium samples of a dog heart failure model. Control: animal without pacing; paced: animal with pacing.
Figure 7:
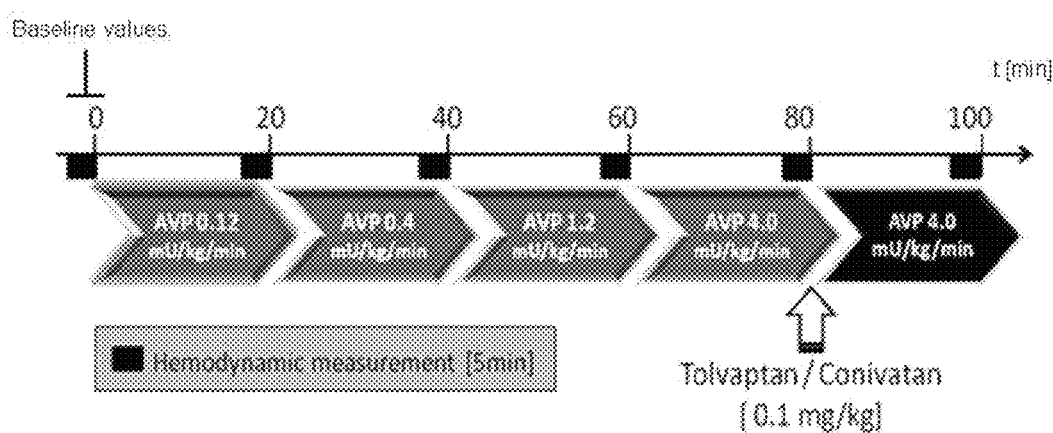
FIG. 7 shows the acute experimental setup for the pacing-induced heart failure model in dogs (according to Yatsu et al., Pharmacol Res 2002; 46:375-381 and Mondritzki et al. Am J. Ther. 2010 Dec 29.)

1. Zhao Q, Jia Y, Xiao Y., Biochem Biophys Res Commun. 2009 Mar. 20; 380(4):721-3
2. Lecaille F, Bromme D, Lalmanach G.; Biochimie. 2008 February; 90(2): 208-26. Epub 2007 Sep. 2.
3. G. E. D'Alonzo et al., Ann. Intern. Med. 1991, 115, 343-349
4. Ghofrani et al., Herz 2005, 30, 296-302
5. M. E. Campian et al., Naunyn-Schmiedeberg's Arch. Pharmacol 2006, 373, 391-400
6. U.S. Euler and G. Liljestrand, Acta Physiol Scand 1946, 12, 301-320
7. N. Weissmann et al., Am. J. Physiol. Lung Cell Mol. Physiol. 2001, 281, L314-L317
8. N. F. Voelkel and R. M. Tuder, J. Clin. Invest. 2000, 106, 733-738
9. Sinha S, Heagerty A M, Shuttleworth C A, Kielty C M., 2002, Cardiovasc Res. March; 53(4):971-83.
10. Watkins S J, Jonker L, Arthur H M., 2006, Cardiovasc Res. February 1; 69(2):432-9.
11. Potter L R, Yoder A R, Flora D R, Antos L K, Dickey D M (2009). Handb Exp Pharmacol 191 (191): 341-66
WO 2004/007477
WO 2006/076796
WO 01/58886
WO 01/070232
WO 00/038687
WO 00/55126
WO 03/075836
WO 2007/003056
WO 99/11640
WO 2004/096785
WO 2004/075835
WO 02/068579

The invention claimed is:
1. A method of treatment of pulmonary hypertension comprising administering an effective amount of a Cathepsin K inhibitor to a human or animal in need thereof, wherein the Cathepsin K inhibitor is a compound of formula (I) to (XIV) or (XV)
| Compound | Structure Name |
|---|---|
| (I) | 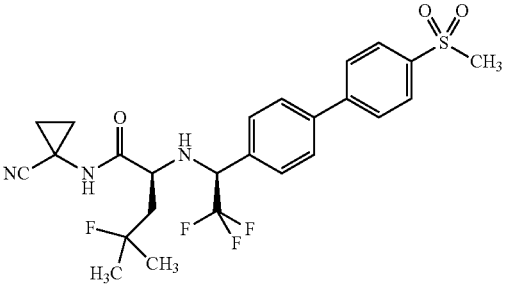 Odanacatib |
| (II) | 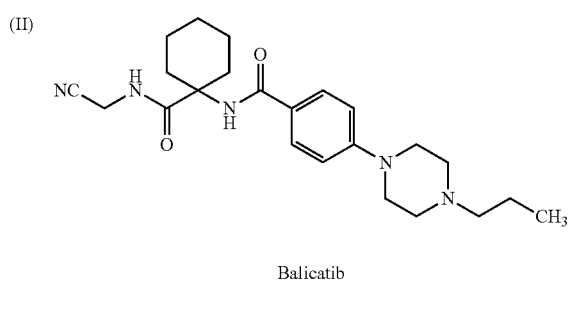 Balicatib |
| (III) | 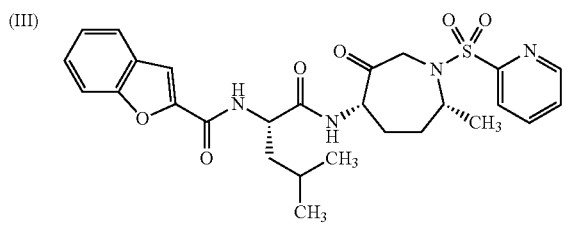 Relacatib |
| (IV) | 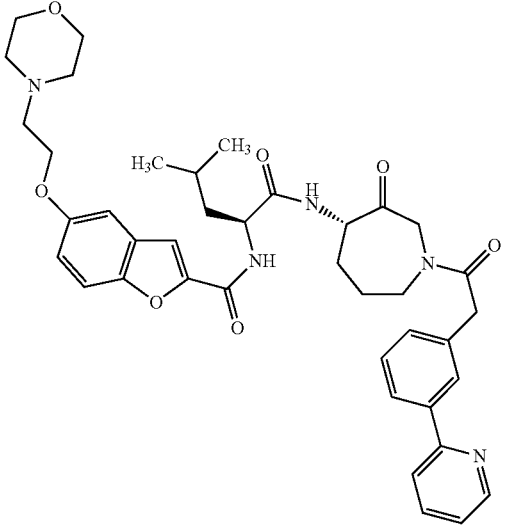 SB-331750 |
| (V) | 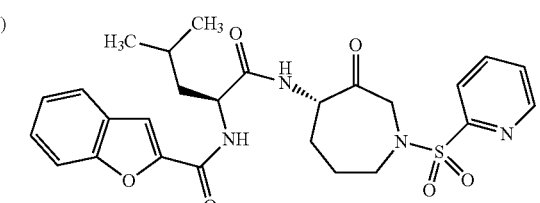 SB-357114 |
| (VI) | 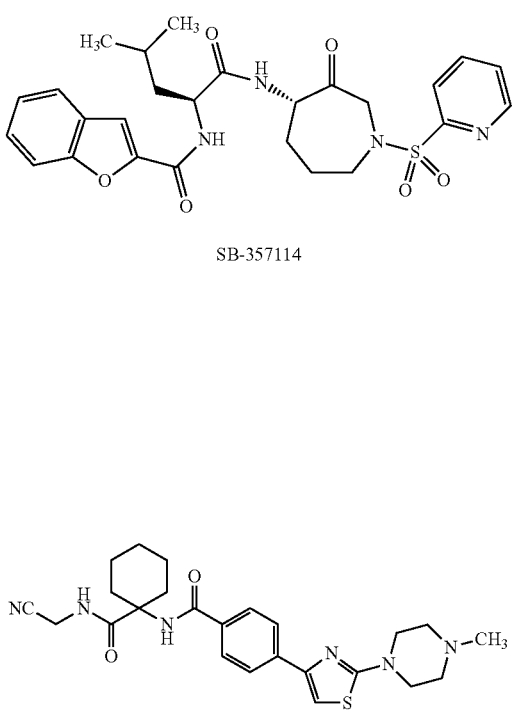 L-006235 |

| Compound | Structure Name |
|---|---|
| (VII) | 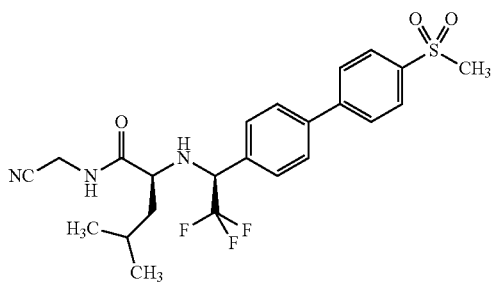<br>L-873742 |
| (VIII) | 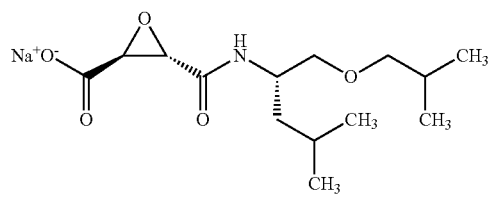<br>NC-2300 |
| (IX) | 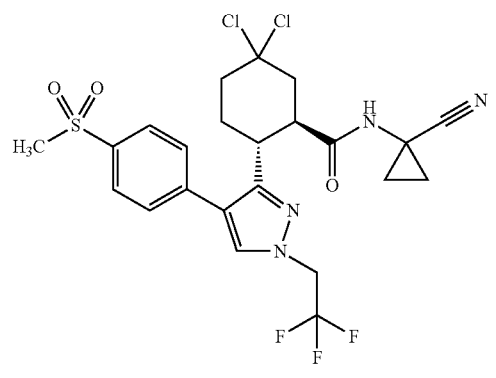<br>MK 1256 |

MIV 701 (X), Ono 5334 (XI), RO 4383315 (XII), SAR-114137 (XIII), MIV 710 (XIV), or MIV 711 (XV).

2. The method of claim 1, wherein the Cathepsin K inhibitor is a compound of formula (I)

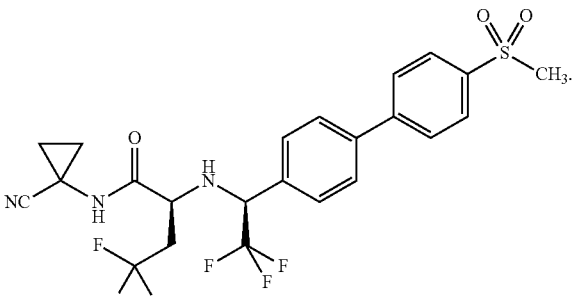

Odanacatib

3. A method of treatment of pulmonary hypertension comprising administering to a human or animal in need thereof an effective amount of a compound of formula (I)

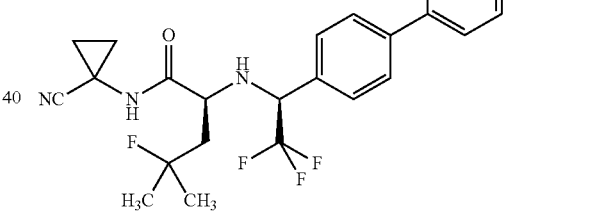

Odanacatib or a salt thereof.

4. The method of claim 1, wherein the Cathepsin K inhibitor is administered orally.

5. A method for treatment of pulmonary hypertension in humans and animals comprising administering to a human or animal a therapeutically effective amount of a pharmaceutical composition comprising at least one Cathepsin K inhibitor and an inert, non-toxic, pharmaceutically acceptable additive, wherein the Cathepsin K inhibitor is a compound of formula (I) to (XIV) or (XV)

| Compound | Structure Name |
|---|---|
| (I) | 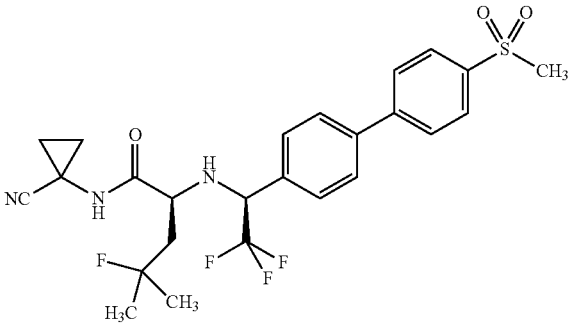<br>Odanacatib |
| (II) | 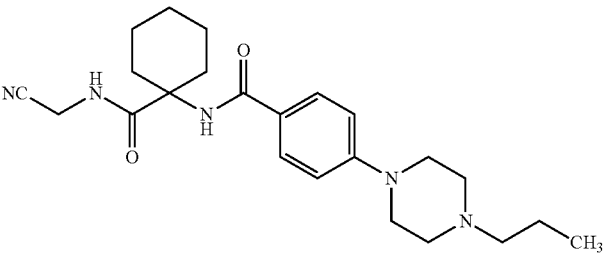<br>Balicatib |
| (III) | 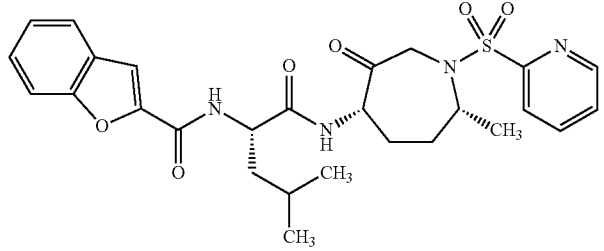<br>Relacatib |
| (IV) | 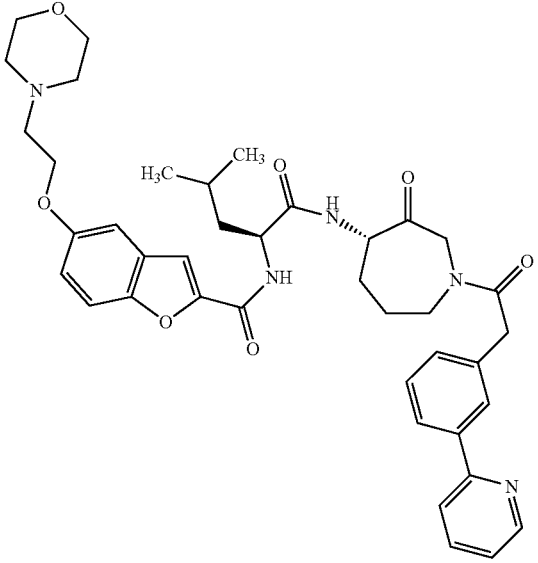<br>SB-331750 |

-continued
| Compound | Structure Name |
|---|---|
| (V) | 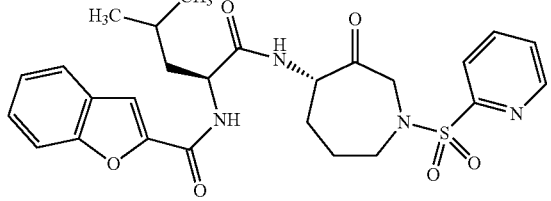  SB-357114 |
| (VI) | 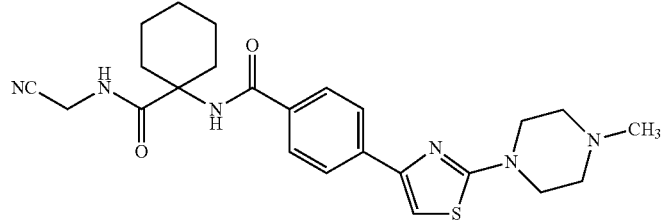  L-006235 |
| (VII) | 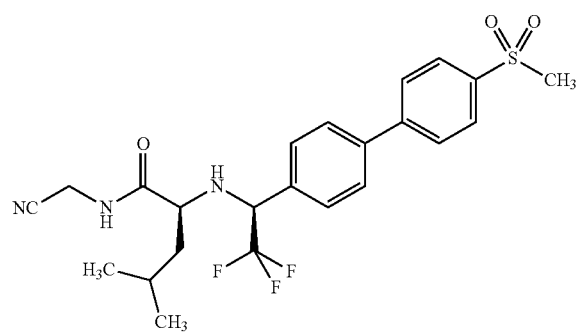  L-873742 |
| (VIII) | 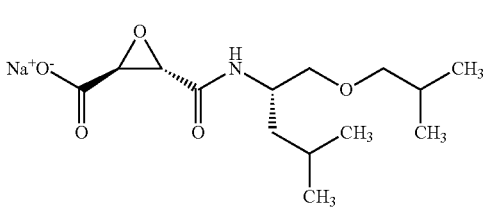  NC-2300 |
| (IX) | 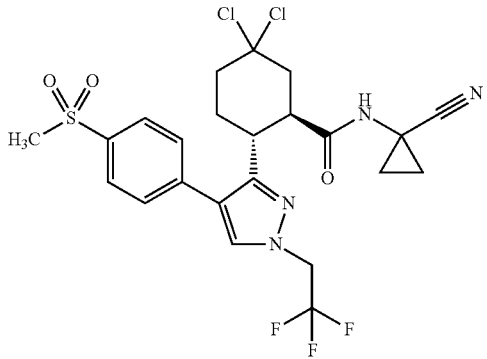  MK 1256 |

MIV 701 (X), Ono 5334 (XI), RO 4383315 (XII), SAR-114137 (XIII), MIV 710 (XIV), or MIV 711 (XV).
6. The method of claim 5, wherein the Cathepsin K inhibitor is a compound of formula (I)
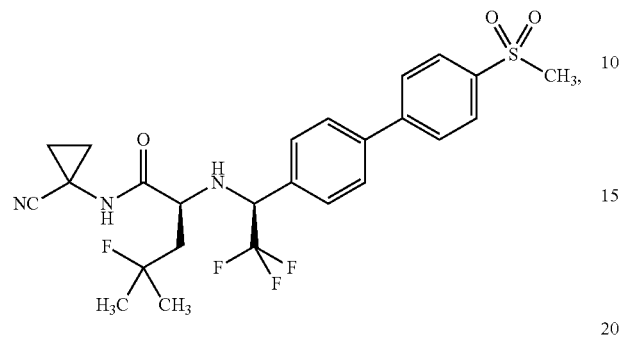
Odanacatib
* * * * *

SEQUENCE LISTING

```
<160> NUMBER OF SEQ ID NOS: 23

<210> SEQ ID NO 1
<211> LENGTH: 990
<212> TYPE: DNA
<213> ORGANISM: Cavia porcellus

<400> SEQUENCE: 1 atgtggggc tcaaggttct gctgctgcct gtggtgagct ttgctctgta ccctgaggag      60
atactggaca ctcagtggga gctttggaag aagacctaca ggaagcagta caatggcaag     120
gtggatgaaa tctctcggcg cataatttgg gaaaagaatc tgaaatatat ttccatccat     180
aaccttgagg cctctcttgg tgtccataca tatgaactga gcatgaacca cttgggagac     240
atgaccagtg aagaagtggt tcagaagatg actgggctca aagtacctcc ctctcattct     300
cacagtaatg ataccctgta catcccagac tgggaaggca gggctcctga ttctgttgac     360
taccgaaaga agggctatgt tactcccgtc aaaaaccagg gtcagtgtgg ttcctgttgg     420
gctttcagct ctgtgggtgc cctcgagggc cagctcaaga agaaaacagg caaactctta     480
aatctgagcc cccagaatct ggtggattgt gtatctgaga atgatggctg tggaggtggc     540
tatatgacca acgcctttca gtatgtgcaa gagaaccgtg gcattgactc tgaggacgcc     600
tatccctacg tgggccagga ggaaagctgt atgtacaatc aacaggcaa ggctgctaaa      660 tgccgcgggt atagagagat ccctgtgggc aatgagaagg cgctgaaaag agctgtggcc     720 cgcgtggac ccgtctctgt ggccattgat gcaagcctga gctccttcca gttctacagc      780
aagggtgtgt attatgatga aagctgcaat ggtgaggatc tgaatcatgc actgctggca     840
```

```
gtgggatatg ggatgcagag aggaaataag cactggatac ttaaaaacag ctggggagaa      900
aactggggaa acaaaggcta tgttctcttg gctcgaaata agaacaatgc atgtggcatt      960
gccaacctcg ccagctttcc caagatgtga                                        990
```

```
<210> SEQ ID NO 2
<211> LENGTH: 329
<212> TYPE: PRT
<213> ORGANISM: Cavia porcellus

<400> SEQUENCE: 2
```

| Met | Trp | Gly | Leu | Lys | Val | Leu | Leu | Pro | Val | Val | Ser | Phe | Ala | Leu |
|---|---|---|---|---|---|---|---|---|---|---|---|---|---|---|
| 1 | | | | 5 | | | | | 10 | | | | | 15 |

| Tyr | Pro | Glu | Glu | Ile | Leu | Asp | Thr | Gln | Trp | Glu | Leu | Trp | Lys | Lys | Thr |
|---|---|---|---|---|---|---|---|---|---|---|---|---|---|---|---|
| | | | 20 | | | | | 25 | | | | | 30 | | |

Tyr Arg Lys Gln Tyr Asn Gly Lys Val Asp Glu Ile Ser Arg Arg Ile
             35                  40                  45

Ile Trp Glu Lys Asn Leu Lys Tyr Ile Ser Ile His Asn Leu Glu Ala
 50                  55                  60

Ser Leu Gly Val His Thr Tyr Glu Leu Ser Met Asn His Leu Gly Asp
 65                  70                  75                  80

Met Thr Ser Glu Glu Val Val Gln Lys Met Thr Gly Leu Lys Val Pro
                 85                  90                  95

Pro Ser His Ser His Ser Asn Asp Thr Leu Tyr Ile Pro Asp Trp Glu
            100                 105                 110

Gly Arg Ala Pro Asp Ser Val Asp Tyr Arg Lys Lys Gly Tyr Val Thr
        115                 120                 125

Pro Val Lys Asn Gln Gly Gln Cys Gly Ser Cys Trp Ala Phe Ser Ser
130                 135                 140

Val Gly Ala Leu Glu Gly Gln Leu Lys Lys Thr Gly Lys Leu Leu
145                 150                 155                 160

Asn Leu Ser Pro Gln Asn Leu Val Asp Cys Val Ser Glu Asn Asp Gly
                165                 170                 175

Cys Gly Gly Gly Tyr Met Thr Asn Ala Phe Gln Tyr Val Gln Glu Asn
            180                 185                 190

Arg Gly Ile Asp Ser Glu Asp Ala Tyr Pro Tyr Val Gly Gln Glu Glu
        195                 200                 205

Ser Cys Met Tyr Asn Pro Thr Gly Lys Ala Ala Lys Cys Arg Gly Tyr
210                 215                 220

Arg Glu Ile Pro Val Gly Asn Glu Lys Ala Leu Lys Arg Ala Val Ala
225                 230                 235                 240

Arg Val Gly Pro Val Ser Val Ala Ile Asp Ala Ser Leu Ser Ser Phe
                245                 250                 255

Gln Phe Tyr Ser Lys Gly Val Tyr Tyr Asp Glu Ser Cys Asn Gly Glu
            260                 265                 270

Asp Leu Asn His Ala Leu Leu Ala Val Gly Tyr Gly Met Gln Arg Gly
        275                 280                 285

Asn Lys His Trp Ile Leu Lys Asn Ser Trp Gly Glu Asn Trp Gly Asn
290                 295                 300

Lys Gly Tyr Val Leu Leu Ala Arg Asn Lys Asn Asn Ala Cys Gly Ile
305                 310                 315                 320

Ala Asn Leu Ala Ser Phe Pro Lys Met
                325

```
<210> SEQ ID NO 3
```

-continued

```
<211> LENGTH: 20
<212> TYPE: DNA
<213> ORGANISM: Cavia porcellus

<400> SEQUENCE: 3
tgagaatgat ggctgtggag                                                  20

<210> SEQ ID NO 4
<211> LENGTH: 20
<212> TYPE: DNA
<213> ORGANISM: Cavia porcellus

<400> SEQUENCE: 4
gtcaatgcca cggttctctt                                                  20

<210> SEQ ID NO 5
<211> LENGTH: 25
<212> TYPE: DNA
<213> ORGANISM: Cavia porcellus

<400> SEQUENCE: 5
atgaccaacg cctttcagta tgtgc                                            25

<210> SEQ ID NO 6
<211> LENGTH: 18
<212> TYPE: DNA
<213> ORGANISM: Cavia porcellus

<400> SEQUENCE: 6
gagtctgcgc aggtccag                                                    18

<210> SEQ ID NO 7
<211> LENGTH: 18
<212> TYPE: DNA
<213> ORGANISM: Cavia porcellus

<400> SEQUENCE: 7
ctgctctggg ctccaatc                                                    18

<210> SEQ ID NO 8
<211> LENGTH: 21
<212> TYPE: DNA
<213> ORGANISM: Cavia porcellus

<400> SEQUENCE: 8
cttcggaggc cggatggaca g                                                21

<210> SEQ ID NO 9
<211> LENGTH: 20
<212> TYPE: DNA
<213> ORGANISM: Cavia porcellus

<400> SEQUENCE: 9
gtgagaatgg acgctgtgtg                                                  20

<210> SEQ ID NO 10
<211> LENGTH: 18
<212> TYPE: DNA
<213> ORGANISM: Cavia porcellus

<400> SEQUENCE: 10
aagccctcga agcagtca                                                    18
```

```
<210> SEQ ID NO 11
<211> LENGTH: 21
<212> TYPE: DNA
<213> ORGANISM: Cavia porcellus

<400> SEQUENCE: 11
cgtgcgggag ggctacacct g                                              21

<210> SEQ ID NO 12
<211> LENGTH: 18
<212> TYPE: DNA
<213> ORGANISM: Cavia porcellus

<400> SEQUENCE: 12
tgtcttcccc tccatcgt                                                  18

<210> SEQ ID NO 13
<211> LENGTH: 20
<212> TYPE: DNA
<213> ORGANISM: Cavia porcellus

<400> SEQUENCE: 13
ttctggccca tgcctaccat                                                20

<210> SEQ ID NO 14
<211> LENGTH: 20
<212> TYPE: DNA
<213> ORGANISM: Cavia porcellus

<400> SEQUENCE: 14
aagatctggc ccttgaacct                                                20

<210> SEQ ID NO 15
<211> LENGTH: 19
<212> TYPE: DNA
<213> ORGANISM: Canis familiaris

<400> SEQUENCE: 15
ggcaccagtc agaccgata                                                 19

<210> SEQ ID NO 16
<211> LENGTH: 20
<212> TYPE: DNA
<213> ORGANISM: Canis familiaris

<400> SEQUENCE: 16
cctattgtca atgcctctgg                                                20
```

-continued

<210> SEQ ID NO 17
<211> LENGTH: 25
<212> TYPE: DNA
<213> ORGANISM: Canis familiaris

<400> SEQUENCE: 17
caaaattaag cgcaactggc ggaaa                                      25

<210> SEQ ID NO 18
<211> LENGTH: 19
<212> TYPE: DNA
<213> ORGANISM: Canis familiaris

<400> SEQUENCE: 18
ggggagaaaa ctggggaaa                                             19

<210> SEQ ID NO 19
<211> LENGTH: 19
<212> TYPE: DNA
<213> ORGANISM: Canis familiaris

<400> SEQUENCE: 19
gccgcaagcg ttgttctta                                             19

<210> SEQ ID NO 20
<211> LENGTH: 26
<212> TYPE: DNA
<213> ORGANISM: Canis familiaris

<400> SEQUENCE: 20
aaaggctata tcctcatggc tcggaa                                     26

<210> SEQ ID NO 21
<211> LENGTH: 20
<212> TYPE: DNA
<213> ORGANISM: Canis familiaris

<400> SEQUENCE: 21
ttggaggaca agatgccttt                                            20

<210> SEQ ID NO 22
<211> LENGTH: 20
<212> TYPE: DNA
<213> ORGANISM: Canis familiaris

<400> SEQUENCE: 22
cttccgcatt ctgctcactc                                            20

<210> SEQ ID NO 23
<211> LENGTH: 25
<212> TYPE: DNA
<213> ORGANISM: Canis familiaris

<400> SEQUENCE: 23
aagatgaagc cgagtctccc caagc                                      25